(12) United States Patent
Kobayashi

(10) Patent No.: US 6,884,891 B2
(45) Date of Patent: Apr. 26, 2005

(54) METHINE DYES, MANUFACTURING METHODS THEREOF, AND SILVER HALIDE PHOTOGRAPHIC MATERIALS CONTAINING SAME DYES

(75) Inventor: Katsumi Kobayashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/192,590

(22) Filed: Jul. 11, 2002

(65) Prior Publication Data

US 2003/0134237 A1 Jul. 17, 2003

(30) Foreign Application Priority Data

Jul. 16, 2001 (JP) .................................... P.2001-215424

(51) Int. Cl.⁷ ............................................. C09B 23/00
(52) U.S. Cl. ...................... 548/156; 548/159; 548/219
(58) Field of Search ............................... 548/156, 159, 548/219

(56) References Cited

U.S. PATENT DOCUMENTS

| | | | | | |
|---|---|---|---|---|---|
| 2,988,544 | A | * | 6/1961 | Frey et al. ................... | 534/812 |
| 3,808,194 | A | * | 4/1974 | Piler et al. ................... | 534/818 |
| 3,838,145 | A | * | 9/1974 | Altermatt .................... | 534/829 |
| 4,339,240 | A | * | 7/1982 | Patel .......................... | 436/171 |
| 4,581,445 | A | * | 4/1986 | Ramanathan ............... | 534/608 |
| 5,032,500 | A | * | 7/1991 | Ikeda et al. ................. | 430/570 |
| 5,275,924 | A | * | 1/1994 | Devonald et al. ........ | 430/495.1 |
| 5,684,139 | A | * | 11/1997 | Wild et al. .................. | 534/797 |
| 5,756,740 | A | | 5/1998 | Vishwakarma et al. | |
| 5,831,039 | A | * | 11/1998 | Schumacher ................ | 534/634 |

FOREIGN PATENT DOCUMENTS

| | | | |
|---|---|---|---|
| EP | 0 887 700 A1 | | 12/1998 |
| GB | 2209468 | * | 5/1989 |
| JP | 2001-305690 | * | 11/2001 |

OTHER PUBLICATIONS

Song et al., Journal of the American Chemical Society, 117(29), 7816–7817, 1995.*
Yarmoluk et al., Dyes and Pigments, 50(1), 21–28, Jul. 11, 2001.*

* cited by examiner

Primary Examiner—Fiona T. Powers

(57) ABSTRACT

Methine dye compounds represented by formula (1) and highly sensitive silver halide photographic materials containing these compounds:

$$\text{Dye1-}(L_1\text{-}(Dye2)_{m1})_{m2} (CI_1)_{y1} \quad (1)$$

wherein $L_1$ represents a linkage group represented by formula (2), m1 represents an integer of 1 to 5, m2 represents an integer of 1 to 5, Dye1 represents a first chromophore, Dye 2 represents a second chromophore, $CI_1$ represents an ion for neutralization of electric charge, and y1 represents a number of the ions required for neutralization of electric charges;

$$\text{-}G_1\text{-}A_1\text{-}Y_1\text{-}G_2\text{-}Y_2\text{-}A_2\text{-}G_3\text{-} \quad (2)$$

wherein $A_1$ and $A_2$ each individually represent a carbonyl group or a sulfonyl group, $Y_1$ and $Y_2$ each individually represent —O—, —S— or —$NR_1$—, $R_1$ represents a hydrogen atom, an alkyl group, an alkenyl group, an aryl group or a heterocyclic group, and $G_1$, $G_2$ and $G_3$ each individually represent a divalent linkage group.

4 Claims, No Drawings

METHINE DYES, MANUFACTURING METHODS THEREOF, AND SILVER HALIDE PHOTOGRAPHIC MATERIALS CONTAINING SAME DYES

FIELD OF THE INVENTION

The present invention relates to methine dye compounds, particularly to coupled-type methine dye compounds having a structure wherein two chromophores are coupled to each other. Further, the present invention is concerned with manufacturing methods of such dye compounds, synthesis intermediates of those dye compounds, and silver halide photographic materials containing those dye compounds.

BACKGROUND OF THE INVENTION

Methine compounds have so far been utilized as spectral sensitizing dyes for silver halide photographic materials. Well-known techniques to enhance light absorptivity of silver halide grains are described below. For improving light absorptivity per one grain, it is required to heighten the density of sensitizing dye molecules adsorbed to each surface of silver halide grains. However, general spectral sensitizing dyes adsorb to the grain surface in a nearly close-packed monolayer, and further adsorption thereof does not occur.

In order to solve this problem, several proposals have been offered. For instance, in *Photographic Science and Engineering*, vol. 20, No. 3, p. 97 (1976), P. B. Gilman Jr. et al. proposed that the first layer is formed by adsorption of a cationic dye and further an anionic dye is made to adsorb through electrostatic force to form the second layer. G. B. Bird et al. disclosed in U.S. Pat. No. 3,622,316 that plural kinds of dyes were adsorbed to each of silver halide grains in a multilayer and sensitization was caused by the contribution of Forster-type excited energy transfer.

In Japanese Patent Application (Laid-Open) Nos. 138341/1988 and 84244/1989, Sugimoto et al. disclosed that spectral sensitization was effected by energy transfer from luminescent dyes.

Although all of these proposals are attempts to adsorb dyes to silver halide grains in an amount greater than saturated adsorption capacity, the sensitizing effect obtained in each proposal was not appreciable, instead, a problem of increasing in intrinsic desensitization came up.

On the other hand, the two-component coupled dyes wherein at least two non-conjugate dye chromophores are coupled to each other via covalent bonds are described in U.S. Pat. Nos. 2,393,351, 2,425,722, 2,518,732, 2,521,944 and 2,592,196, and European Pat. No. 565,083. Therein, however, improvements in light absorptivity are not aimed at. Attempts to positively aim at improving light absorptivity are disclosed by G. B. Bird et al. in U.S. Pat. Nos. 3,622,317 and 3,976,493. Therein, molecules of a coupled-type sensitizing dye having a plurality of cyanine chromophores are made to adsorb, thereby intending enhancement of the light absorptivity and sensitization by energy transfer. However, these attempts fail to achieve a noticeable improvement in sensitivity.

In Japanese Patent Application (Laid-Open) No. 91134/1989, Ukai et al. proposes to combine at least one dye which is substantially non-adsorptive but contains at least two sulfo or carboxyl groups with a spectral sensitizing dye capable of adsorbing to silver halide grains.

In addition, VishwaKarma et al. disclose in Japanese Patent Application (Laid-Open) No. 27578/1994 the spectral sensitization with two-component coupled dyes formed by coupling silver halide-adsorptive cyanine dyes to non-adsorptive oxonol dyes, and Parton et al. disclose in EP-A1-887700 the spectral sensitization with two-component coupled dyes formed by coupling adsorptive cyanine dyes to non-adsorptive merocyanine dyes via particular linkage groups. However, it cannot be said that a satisfactory increase in sensitivity is caused by contribution of energy transfer.

As described above, any of the methods disclosed in the patents and literature have failed to achieve sufficient increase in sensitivity. Therefore, it is required to further pursue technological development.

Although both cyanine and merocyanine dyes containing benzoxazole nuclei are promising chromophores bearing excellent characteristics as spectral sensitizing dyes for silver halide photographic materials, asymmetric coupled dyes having a benzoxazole nucleus in each of the dyes coupled together have never been synthesized. A reason for this lies in difficulty of synthesizing a dye containing both benzoxazole nucleus and primary amino group in each molecule. In other words, it was difficult to introduce amino groups because of instability of benzoxazole nuclei. Under these circumstances, it has been desired to develop methods of synthesizing dyes containing in each molecule both benzoxazole nucleus and primary amino group.

SUMMARY OF THE INVENTION

Therefore, the objects of the present invention are to provide novel dye compounds, manufacturing methods thereof and highly sensitive silver halide photographic materials containing such dye compounds.

The objects of the present invention are achieved by the following Embodiments (1) to (21).

(1) A compound represented by formula (1):

$$\text{Dye1-}(L_1\text{-}(Dye2)_{m1})_{m2}\,(CI_1)_{y1} \tag{1}$$

wherein $L_1$ represents a linkage group represented by formula (2), m1 represents an integer of 1 to 5, m2 represents an integer of 1 to 5, Dye1 represents a first chromophore, Dye2 represents a second chromophore, $CI_1$ represents an ion for neutralization of electric charge, and y1 represents a number of the ions required for neutralization of electric charges;

$$\text{-}G_1\text{-}A_1\text{-}Y_1\text{-}G_2\text{-}Y_2\text{-}A_2\text{-}G_3\text{-} \tag{2}$$

wherein $A_1$ and $A_2$ each individually represent a carbonyl group or a sulfonyl group, $Y_1$ and $Y_2$ each individually represent —O—, —S— or —$NR_1$—, $R_1$ represents a hydrogen atom, an alkyl group, an alkenyl group, an aryl group or a heterocyclic group, and $G_1$, $G_2$ and $G_3$ each individually represent a divalent linkage group.

(2) A compound represented by formula (3):

$$\text{Dye3-}G_4\text{-}A_3\text{-}Y_3\text{-}G_5\text{-}Y_4\text{-H}\,(CI_2)_{y2} \tag{3}$$

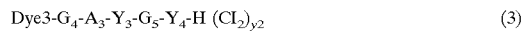

wherein Dye3 represents a chromophore, $Y_4$ represents —NH—, —$NH_2^+$—, —S— or —O—, $A_3$ represents a carbonyl group or a sulfonyl group, $Y_3$ represents —O—, —S— or —$NR_1$—, $R_1$ represents a hydrogen atom, an alkyl group, an alkenyl group, an aryl group or a heterocyclic group, $G_4$ and $G_5$ each individually represent a divalent linkage group, $CI_2$ represents an ion for neutralization of electric charge, and y2 represents a number of the ions required for neutralization of electric charges.

(3) A compound represented by formula (1) or (3), wherein at least one of the chromophores Dye1, Dye2 and Dye3 is a cyanine dye, a merocyanine dye or an oxonol dye.

(4) A compound represented by formula (1) or (3), wherein all of the chromophores Dye1, Dye2 and Dye3 are any of cyanine dyes, merocyanine dyes and oxonol dyes.

(5) A method of manufacturing a compound of formula (1) as defined in Embodiment (1) by causing a reaction between a compound of formula (3) as defined in Embodiment (2) and a compound represented by formula (4):

$$\text{Dye4-G}_6\text{-A}_4\text{-Y}_5 \text{ (Cl}_3)_{y3} \tag{4}$$

wherein Dye4 represents a chromophore, $A_4$ represents a caronyl group or a sulfonyl group, $G_6$ represents a divalent linkage group, $Y_5$ represents a hydroxyl group, a halogen atom, an alkoxy group, an aryloxy group, an acyloxy group, an alkyl- or arylsulfonyloxy group, an alkyl- or aryloxycarbonyloxy group, an imidyloxycarbonyloxy group or a heterocyclic group, $Cl_3$ represents an ion for neutralization of electric charge, and y3 represents a number of the ions required for neutralization of electric charges.

(6) A manufacturing method as described in Embodiment (5), wherein $Y_5$ in formula (4) is a hydroxyl group and the reaction is carried out in the presence of a condensing agent.

(7) A compound represented by formula (5):

$$\text{Dye3-G}_4\text{-A}_3\text{-Y}_3\text{-G}_5\text{-Y}_4\text{-P (Cl}_4)_{y4} \tag{5}$$

wherein Dye3, $A_3$, $G_4$, $G_5$, $Y_3$ and $Y_4$ have the same meanings as in formula (3) respectively, P represents a protective group, $Cl_4$ represents an ion for neutralization of electric charge, and y4 is a number of the ions required for neutralization of electric charges.

(8) A compound represented by formula (5), wherein the chromophore Dye3 represents a cyanine dye, a merocyanine dye or an oxonol dye.

(9) A compound represented by formula (5), wherein the protective group P represents a t-butoxycarbonyl group, a substituted or unsubstituted benzylidene group, a triarylmethyl group or a benzyloxycarbonyl group.

(10) A method of manufacturing a compound of formula (3) by removing the protective group P from the compound of formula (5).

(11) The method of manufacturing the compound as described in Embodiment (10), wherein the protective group P in formula (5) is a t-butoxycarbonyl group, a substituted or unsubstituted benzylidene group, a triarylmethyl group or a benzyloxycarbonyl group.

(12) The manufacturing method as described in Embodiment (10), wherein the protective group P is removed from the compound represented by formula (5) under an acid condition.

(13) A method of manufacturing a compound represented by formula (5) as defined in Embodiment (7) by causing a reaction between a compound represented by formula (6) and a compound represented by formula (7):

$$\text{Dye3-G}_4\text{-A}_3\text{-Y}_6 \text{ (Cl}_5)_{y5} \tag{6}$$

$$\text{HY}_3\text{-G}_5\text{-Y}_4\text{-P} \tag{7}$$

wherein Dye3, $A_3$ and $G_4$ have the same meanings as in formula (3), respectively; $Y_6$ represents a hydroxyl group, a halogen atom, an alkoxy group, an aryloxy group, an acyloxy group, an alkyl- or arylsulfonyloxy group, an alkyl- or aryloxycarbonyloxy group, or a heterocyclic group; $Cl_5$ represents an ion for neutralization of electric charge; y5 is a number of the ions required for neutralization of electric charges; and $Y_3$, $Y_4$, $G_5$ and P have the same meanings as in formula (5), respectively.

(14) A silver halide photographic material comprising a support having thereon at least one light-sensitive silver halide emulsion layer, the emulsion layer containing a compound of formula (1) as defined in Embodiment (1), (3) or (4), a compound of formula (3) as defined in Embodiment (2), (3) or (4), or a compound of formula (5) as defined in Embodiment (7), (8) or (9).

(15) The compound represented by formula (1) as defined in Embodiment (1), wherein at least one of Dye1 and Dye2 is a cyanine or merocyanine chromophore having at least one benzoxazole nucleus.

(16) The compound represented by formula (5) as defined in Embodiment (7), (8) or (9), wherein Dye3 is a cyanine or merocyanine chromophore containing at least one benzoxazole nucleus.

(17) The compound represented by formula (1) as defined in Embodiment (1) and a compound represented by formula (5) as defined in Embodiment (7), (8) or (9), wherein Dye1, Dye2 and Dye3 are each a cyanine or merocyanine chromophore containing at least one benzoxazole nucleus.

(18) A cyanine or merocyanine dye compound containing in a molecule at least one primary amino group as a substituent and at least one bezoxazole nucleus.

(19) The compound represented by formula (3) as defined in Embodiment (2), (3) or (4), wherein Dye3 is a cyanine or merocyanine chromophore containing at least one benzoxazole nucleus.

(20) The manufacturing method as defined in Embodiment (5), (6), (10), (11), (12) or (13), wherein each of Dye1, Dye2, Dye3 and Dye4 is a cyanine or merocyanine chromophore containing at least one benzoxazole nucleus.

(21) A silver halide photographic material comprising a support having thereon at least one light-sensitive silver halide emulsion layer, the emulsion layer containing a compound of formula (1) as defined in Embodiment (15), a compound of formula (3) as defined in Embodiment (19), a compound of formula (5) as defined in Embodiment (16) or (17), or a compound as defined in Embodiment (18).

DETAILED DESCRIPTION OF THE INVENTION

Firstly, compounds represented by formulae (1), (3) and (5), respectively, which are compounds relating to the present invention, are described in detail. In silver halide photographic materials, it is advantageous to use at least one compound represented by formula (1), (3) or (5). And it is more advantageous to use at least one compound represented by formula (1) or (3), especially a compound represented by formula (1).

The present compounds are illustrated below in detail.

Additionally, when the present compounds contain alkyl, alkylene, alkenyl or alkenylene groups, these groups each may have a linear or branched structure and may be substituted or not, unless otherwise indicated.

Further, when the present compounds contain cycloalkyl, aryl, heterocyclic, cycloalkenylene, arylene or heterylene groups, these groups each may be a single or condensed ring residue and may have substituents or may not unless otherwise indicated.

In the present invention, the cases where certain moieties are termed groups mean that the moieties in themselves may not be substituted or may have at least one (to the greatest possible number of) substituent.

For instance, the term "alkyl groups" as used in the present invention is intended to include substituted and unsubstituted alkyl groups. And substituents usable for the present compounds (i.e., compounds of the present invention) may include any substituents, irrespective of whether they are substituted or not. Specifically, a substituent group W as described below exemplifies the substituents usable in the present invention.

The substituents represented by W may include any substituents, and have no particular restrictions. Examples thereof include halogen atoms, alkyl groups [including cycloalkyl groups, bicycloalkyl groups, tricycloalkyl groups, alkenyl groups (including cycloalkenyl groups and bicycloalkenyl groups) and alkynyl groups], aryl groups, heterocyclic groups, a cyano group, a hydroxyl group, a nitro group, a carboxyl group, alkoxy groups, aryloxy groups, silyloxy groups, heterocyclyloxy groups, acyloxy groups, carbamoyloxy groups, alkoxycarbonyloxy groups, aryloxycarbonyloxy groups, amino groups (including anilino groups), ammonio groups, acylamino groups, aminocarbonylamino groups, alkoxycarbonylamino groups, aryloxycarbonylamino groups, sulfamoylamino groups, alkyl- and arylsulfonylamino groups, a mercapto group, alkylthio groups, arylthio groups, heterocyclylthio groups, a sulfamoyl group, a sulfo group, alkyl- and arylsulfinyl groups, alkyl- and arylsulfonyl groups, acyl groups, aryloxycarbonyl groups, alkoxycarbonyl groups, a carbamoyl group, aryl- and heterocyclylazo groups, an imido group, a phosphino group, a phosphinyl group, a phosphinyloxy group, a phosphinylamino group, a phospho group, a silyl group, a hydrazino group, an ureido group, and other known substituents.

In more detail, the substituent group W includes halogen atoms (e.g., fluorine, chlorine, bromine and iodine atoms), alkyl groups [including linear, branched and cyclic alkyl groups which may have substituents or may not, with examples including alkyl groups (preferably containing 1 to 30 carbon atoms, such as methyl, ethyl, n-propyl, isopropyl, t-butyl, n-octyl, eicosyl, 2-chloroethyl, 2-cyanoethyl and 2-ethylhexyl), cycloalkyl groups (preferably $C_{3-30}$ substituted or unsubstituted cycloalkyl groups, such as cyclohexyl, cyclopentyl and 4-n-dodecylcyclohexyl), bicycloalkyl groups (preferably $C_{5-30}$ substituted or unsubstituted bicycloalkyl groups, namely monovalent groups formed by removing one hydrogen atom from each individual $C_{5-30}$ bicycloalkanes, such as bicyclo[1,2,2]heptane-2-yl and bicyclo[2,2,2]octane-3-yl), and alkyl groups having more ring structures, such as tricycloalkyl groups; the concept of which fits the alkyl groups in substituents described below (e.g., the alkyl groups in alkylthio groups)], alkenyl groups [specifically, linear, branched and cyclic alkenyl groups which may be substituted or may not, with examples including alkenyl groups (preferably $C_{2-30}$ substituted or unsubstituted alkenyl groups, such as vinyl, allyl, pulenyl, geranyl and oleyl), cycloalkenyl groups (preferably $C_{3-30}$ substituted or unsubstituted cycloalkenyl groups, namely monovalent groups formed by removing one hydrogen atom from each individual $C_{3-30}$ cycloalkenes, such as 2-cyclopentene-1-yl and 2-cyclohexene-1-yl) and bicycloalkenyl groups (including substituted and unsubstituted bicycloalkenyl groups, preferably $C_{5-30}$ substituted and unsubstituted bicycloalkenyl groups, namely monovalent groups formed by removing one hydrogen atom from each individual bicycloalkenes having one double bond per one molecule, such as bicyclo[2,2,1]hepto-2-ene-1-yl and bicyclo[2,2,2]octo-2-ene-4-yl)], alkynyl groups (preferably $C_{2-30}$ substituted and unsubstituted alkynyl groups, such as ethynyl, propargyl and trimethylsilylethynyl groups), aryl groups (preferably $C_{6-30}$ substituted and unsubstituted aryl groups, such as phenyl, p-tolyl, naphthyl, m-chlorophenyl and o-hexadecanoylaminophenyl), heterocyclic groups (preferably monovalent groups formed by removing one hydrogen atom from each individual 5- or 6-membered, substituted or unsubstituted aromatic or non-aromatic heterocyclic compounds, particularly preferably $C_{3-30}$ 5- or 6-membered aromatic heterocyclic groups, such as 2-furyl, 2-thienyl, 2-pyrimidyl and 2-benzothiazolyl groups, wherein cationic heterocyclic groups, such as 1-methyl-2-pyridinio and 1-methyl-2-quinolinio groups, may additionally be included), a cyano group, a hydroxyl group, a nitro group, a carboxyl group, alkoxy groups (preferably $C_{1-30}$ substituted and unsubstituted alkoxy groups, such as methoxy, ethoxy, isopropoxy, t-butoxy, n-octyloxy and 2-methoxyethoxy), aryloxy groups (preferably $C_{6-30}$ substituted or unsubstituted aryloxy groups, such as phenoxy, 2-methylphenoxy, 4-t-butylphenoxy, 3-nitrophenoxy and 2-tetradecanoylaminophenoxy), silyloxy groups (preferably $C_{3-20}$ silyloxy groups, such as trimethylsilyloxy and t-butyldimethylsilyloxy), heterocyclicoxy groups (preferably $C_{2-30}$ substituted and unsubstituted heterocyclicoxy groups, such as 1-phenyltetrazole-5-oxy and 2-tetrahydropyranyloxy), acyloxy groups (preferably including formyloxy group, $C_{2-30}$ substituted and unsubstituted alkylcarbonyloxy groups, and $C_{6-30}$ substituted and unsubstituted aryloxycarbonyloxy groups, such as formyloxy, acetyloxy, pivaroyloxy, stearoyloxy, benzoyloxy and p-methoxyphenylcarbonyloxy), carbamoyloxy groups (preferably $C_{1-30}$ substituted and unsubstituted carbamoyloxy groups, such as N,N-dimethylcarbamoyloxy, N,N-diethylcarbamoyloxy, morpholinocarbonyloxy, N,N-di-n-octylaminocarbonyloxy and N-n-octylcarbamoyloxy), alkoxycarbonyloxy groups (preferably $C_{2-30}$ substituted and unsubstituted alkoxycarbonyloxy groups, such as methoxycarbonyloxy, ethoxycarbonyloxy, t-butoxycarbonyloxy and n-octylcarbonyloxy), aryloxycarbonyloxy groups (preferably $C_{7-30}$ substituted and unsubstituted aryloxycarbonyloxy groups, such as phenoxycarbonyloxy, p-methoxyphenoxycarbonyloxy and p-n-hexadecyloxyphenoxy-carbonyloxy), amino groups (preferably including an amino group, $C_{1-30}$ substituted and unsubstituted alkylamino groups and $C_{6-30}$ substituted and unsubstituted anilino groups, such as amino, methylamino, dimethylamino, anilino, N-methyl-anilino and diphenylamino), ammonio groups (preferably including an ammonio group and $C_{1-30}$ substituted or unsubstituted alkyl, aryl and hetero ring-substituted ammonio groups, such as trimethylammonio, triethylammonio and diphenylmethylammonio), acylamino groups (preferably including an formylamino group, $C_{1-30}$ substituted or unsubstituted alkylcarbonylamino groups and $C_{6-30}$ substituted or unsubstituted arylcarbonylamino groups, such as formylamino, acetylamino, pivaroylamino, lauroylamino, benzoylamino and 3,4,5-tri-n-octyloxyphenylcarbonylamino), aminocarbonylamino groups (preferably $C_{1-30}$ substituted or unsubstituted aminocarbonylamino groups, such as carbamoylamino, N,N-dimethylaminocarbonylamino, N,N-diethylaminocarbonylamino and morpholinocarbonylamino), alkoxycarbonylamino groups (preferably $C_{2-30}$ substituted or unsubstituted alkoxycarbonylamino groups, such as methoxycarbonylamino, ethoxycarbonylamino, t-butoxycarbonylamino, n-octadecyloxy-carbonylamino and N-methyl-methoxycarbonylamino), aryloxy-carbonylamino groups (preferably $C_{7-30}$ substituted or unsubstituted aryloxycarbonylamino groups, such as phenoxycarbonylamino, p-chlorophenoxycarbonylamino and m-n-octyloxyphenoxycarbonylamino), sulfamoylamino groups (preferably $C_{0-30}$ substituted or unsubstituted sulfamoylamino groups, such as sulfamoylamino, N,N-dimethylaminosulfonylamino and N-n-octylaminosulfonylamino), alkyl- and arylsulfonylamino groups (preferably including $C_{1-30}$ substituted or unsubstituted alkylsulfonylamino and $C_{6-30}$ substituted or unsubstituted arylsulfonylamino groups, such as methylsulfonylamino, butylsulfonylamino, phenylsulfonylamino, 2,3,5-trichlorophenylsulfonylamino and p-methylphenylsulfonylamino), a mercapto group, alkylthio groups (preferably $C_{1-30}$ substituted or unsubstituted alkylthio groups, such as methylthio, ethylthio and n-hexadecylthio), arylthio groups (preferably $C_{6-30}$ substituted or unsubstituted arylthio groups, such as phenylthio, p-chlorophenylthio and m-methoxyphenylthio), heterocyclylthio groups (preferably $C_{2-30}$ substituted or unsubstituted heterocyclylthio groups, such as 2-benzothiazolylthio and 1-phenyltetrazole-5-ylthio), sulfamoyl groups (preferably $C_{0-30}$ substituted or unsubstituted sulfamoyl groups, such as N-ethylsulfamoyl, N-(3-dodecyloxypropyl)sulfamoyl, N,N-diemthylsulfamoyl, N-acetylsulfamoyl, N-benzoylsulfamoyl and N-(N'-phenylcarbamoyl)sulfamoyl), a sulfo group, alkyl- and arylsulfinyl groups (preferably $C_{1-30}$ substituted or unsubstituted alkylsulfinyl group and $C_{6-30}$ substituted or unsubstituted arylsulfinyl groups, such as methylsulfinyl, ethylsulfinyl, phenylsulfinyl and p-methylphenylsulfinyl), alkyl- and arylsulfonyl groups (preferably $C_{1-30}$ substituted or unsubstituted alkylsulfonyl groups and $C_{6-30}$ substituted or unsubstituted arylsulfonyl groups, such as methylsulfonyl, ethylsulfonyl, phenylsulfonyl and p-methylphenylsulfonyl), acyl groups (preferably including a formyl group, $C_{2-30}$ substituted or unsubstituted alkylcarbonyl groups, $C_{7-30}$ substituted or unsubstituted arylcarbonyl groups and $C_{4-30}$ substituted or unsubstituted heterocyclylcarbonyl groups wherein the carbonyl group is attached to a carbon atom, such as acetyl, pivaroyl, 2-chloroacetyl, stearoyl, benzoyl, p-n-octyloxyphenylcarbonyl, 2-pyridylcarbonyl and 2-furylcarbonyl), aryloxycarbonyl groups (preferably $C_{7-30}$ substituted or unsubstituted aryloxycarbonyl groups, such as phenoxycarbonyl, o-chlorophenoxycarbonyl, m-nitrophenoxy-carbonyl and p-t-butylphenoxycarbonyl), alkoxycarbonyl groups (preferably $C_{2-30}$ substituted or unsubstituted alkoxycarbonyl groups, such as methoxycarbonyl, ethoxycarbonyl, t-butoxycarbonyl and n-octadecyloxycarbonyl) carbamoyl groups (preferably $C_{1-30}$ substituted or unsubstituted carbamoyl groups, such as carbamoyl, N-methylcarbamoyl, N,N-dimethylcarbamoyl, N,N-di-n-octylcarbamoyl and N-(methylsulfonyl)carbamoyl), aryl- and heterocyclylazo groups (preferably $C_{6-30}$ substituted or unsubstituted arylazo groups and $C_{3-30}$ substituted or unsubstituted heterocyclicazo groups, such as phenylazo, p-chlorophenylazo and 5-ethylthio-1,3,4-thiadiazole-2-ylazo), imido groups (preferably N-succinimido and N-phthalimido), phosphino groups (preferably $C_{2-30}$ substituted or unsubstituted phosphino groups, such as dimethylphosphino, diphenylphosphino and methylphenoxyphosphino), phosphinyl groups (preferably $C_{2-30}$ substituted or unsubstituted phosphinyl groups, such as phosphinyl, dioctyloxyphosphinyl and diethoxyphosphinyl), phosphinyloxy groups (preferably $C_{2-30}$ substituted or unsubstituted phosphinyloxy groups, such as diphenoxyphosphinyloxy and dioctyloxyphosphinyloxy), phosphinylamino groups (preferably $C_{2-30}$ substituted or unsubstituted phosphinylamino groups, such as dimethoxyphosphinylamino and dimethylaminophosphinylamino), a phospho group, silyl groups (preferably $C_{3-30}$ substituted or unsubstituted silyl groups, such as trimethylsilyl, t-butyldimethylsilyl and phenyldimethylsilyl), hydrazino groups (preferably $C_{0-30}$ substituted or unsubstituted hydrazino groups, such as trimethylhydrazino), and ureido groups (preferably $C_{0-30}$ substituted or unsubstituted ureido groups, such as N,N-dimethylureido).

Certain groups included in the substituent group W can have ring-condensed structures (wherein each ring condensed may be any of aromatic rings, non-aromatic rings and hetero rings, which may further be combined with other rings to form a polycyclic condensed ring, with examples including a benzene ring, a naphthalene ring, an anthracene ring, a quinoline ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine, a quinoline ring, a phthalazine ring, a naphthyridine ring, a quinoxaline ring, a quinoxazoline ring, a quinoline ring, a carbazole ring, a phenanthrolizine ring, an acrylizine ring, a phenanthroline ring, a thianthrene ring, a chromene ring, a xanthene ring, a phenoxthine ring, a phenoxazine ring and a phenazine ring).

In the substituent group W, those containing hydrogen atoms may have the substituents as described above in place of their hydrogen atoms. Examples of such functional groups include alkylcarbonylaminosulfonyl groups, arylcarbonylaminosulfonyl groups, alkylsulfonylaminocarbonyl groups and arylsulfonylaminocarbonyl groups. Specifically, these functional groups include methylsulfonylaminocarbonyl, p-methylphenylsulfonylaminocarbonyl, acetylaminosulfonyl and benzoylaminosulfonyl groups.

In formula (1), m1 represents an integer of 1 to 5, preferably 1 or 2, particularly preferably 1, and m2 represents an integer of 1 to 5, preferably 1 or 2, particularly preferably 1.

Each of Dye1, Dye2, Dye3 and Dye4 represents a chromophore.

The chromophore represented by Dye1, Dye2, Dye3 and Dye4 each may be any of known chromophores, with examples including cyanine dyes, styryl dyes, hemicyanine dyes, merocyanine dyes, trinuclear merocyanine dyes, tetranuclear merocyanine dyes, rhodacyanine dyes, complex cyanine dyes, complex merocyanine dyes, allopolar dyes, oxonol dyes, hemioxonol dyes, squarylium dyes, croconium dyes, azamethine dyes, coumarin dyes, allylidene dyes, anthraquinone dyes, triphenylmethane dyes, azo dyes, azomethine dyes, spiro compounds, metallocene dyes, fluorenone dyes, fulgide dyes, perylene dyes, phenazine dyes, phenothiazine dyes, quinone dyes, indigo dyes, diphenylmethane dyes, polyene dyes, acridine dyes, acridinone dyes, diphenylamine dyes, quinacridone dyes, quinophthalone dyes, phenoxazine dyes, phthaloperylene dyes, porphyrin dyes, chlorophyll dyes, phthalocyanine dyes, and metal complex dyes.

Of these dyes, the dyes used to advantage are polymethine chromophores, such as cyanine dyes, styryl dyes, hemicyanine dyes, merocyanine dyes, trinuclear cyanine dyes, tetranuclear merocyanine dyes, rhodacyanine dyes, complex cyanine dyes, complex merocyanine dyes, allopolar dyes, oxonol dyes, hemioxonol dyes, squarylium dyes, croconium dyes, azamethine dyes and oxonol dyes.

Details of those dyes are described, e.g., in F. M. Harmer, *Heterocyclic Compounds—Cyanine Dyes and Related Compounds*, John Wiley & Sons, New York, London (1964), and D. M. Sturmer, *Heterocyclic Compounds—Special topics in heterocyclic chemistry*, chapter 18, section 14, pages 482–515. The general formulae of preferable dyes include those illustrated in U.S. Pat. No. 5,994,051, from page 32 to page 36, and those illustrated in U.S. Pat. No. 5,747,236, from page 30 to page 34. As examples of general formulae of favorable cyanine, merocyanine and rhodacyanine dyes, those illustrated as formulae (XI), (XII) and (XIII) in U.S. Pat. No. 5,340,694, from column 21 to column 22 (wherein, however, the number represented by n12, n15, n17 and n18 each has no limitation, but it is an integer of no smaller than 0 (preferably no greater than 4) are exemplified.

It is appropriate that each of Dye1, Dye2, Dye3 and Dye4 be any of cyanine, merocyanine and oxonol chromophores, preferably any of cyanine and mercocyanine chromophores. In particular, it is most suitable for Dye1 to be a cyanine chromophore.

When Dye1, Dye2, Dye3 and Dye4 each represent a cyanine chromophore or a merocyanine chromophore, it is favorable that at least one of Dye1, Dye2, Dye3 and Dye4 contains a benzoxazole nucleus in the chromophore. More favorably, at least either Dye1 or Dye2, or each of Dye1 and Dye2 contains a benzoxazole nucleus in its chromophore. In particular, it is advantageous that at least one benzoxazole nucleus is contained in each of the chromophores Dye1, Dye2, Dye3 and Dye4.

It is preferable that Dye2 be substituted with a group containing a water-soluble, non-adsorptive substituent. The water-soluble, non-adsorptive substituent may be any group so long as the group has higher hydrophilicity than alkyl groups, with examples including positively or negatively charged groups and groups containing atoms having lone electron pairs and electronegativity greater than carbon atom. In particular, groups substituted with —$SO_3M$, —$OSO_3M$, —$mPO_3M_2$, —$OPO_3M_2$ and —COOM respectively are preferred as those groups. Herein, M represents a proton or a cation.

The suitable cyanine chromophores are chromophores represented by the following formula (8):

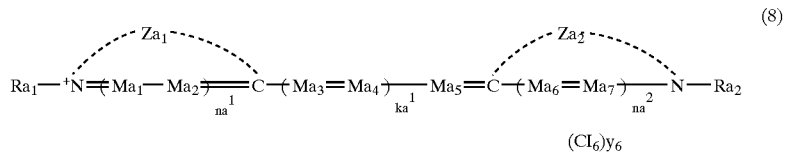

(8)

wherein $Za_1$ and $Za_2$ each represent atoms forming a 5- or 6-membered nitrogen-containing hetero ring, which may be condensed with a benzene ring, a benzofuran ring, a pyridine ring, a pyrrole ring, an indole ring or a thiophene ring; and $Ra_1$ and $Ra_2$ each represent a hydrogen atom, an alkyl group, an alkenyl group, an aryl group or a heterocyclic group. It is favorable that $Ra_1$ and $Ra_2$ each individually represent a hydrogen atom, an alkyl group [preferably a $C_{1-18}$, more preferably $C_{1-7}$, particularly preferably $C_{1-4}$, unsubstituted alkyl group, such as methyl, ethyl, propyl, isopropyl, butyl, isobutyl, hexyl, octyl, 2-ethylhexyl, docecyl and octadecyl, or a $C_{1-18}$, preferably $C_{1-7}$, particularly preferably $C_{1-4}$ substituted alkyl group (examples of which include alkyl groups substituted with W as described above, preferably aralkyl groups (e.g., benzyl, 2-phenylethyl), hydroxyalkyl groups (e.g., 2-hydroxyethyl, 3-hydroxypropyl, 6-hydroxyhexyl), carboxyalkyl groups (e.g., 2-carboxyethyl, 3-carboxypropyl, 4-carboxybutyl, carboxymethyl, 5-carboxypentyl), alkoxyalkyl groups (e.g., 2-methoxyethyl, 2-(2-methoxyethoxy)ethyl), aryloxyalkyl groups (e.g., 2-phenoxyethyl, 2-(1-naphthoxy)ethyl), alkoxycarbonylalkyl groups (e.g., ethoxycarbonylmethyl, 2-benzyloxycarbonylethyl), aryloxycarbonylalkyl groups (e.g., 3-phenoxycarbonylpropyl), acyloxyalkyl groups (e.g., 2-acetyloxyethyl), acylalkyl groups (e.g., 2-acetylethyl), carbamoylalkyl groups (e.g., 2-morpholinocarbonylethyl), sulfamoylalkyl groups (e.g., N,N-dimethylsulfamoylmethyl), sulfoalkyl groups (e.g., 2-sulfobenzyl, 3-sulfo-3-phenylpropyl, 2-sulfoethyl, 3-sulfopropyl, 3-sulfobutyl, 4-sulfobutyl, 2-(3-sulfopropoxy)ethyl, 2-hydroxy-3-sulfopropyl, 3-sulfopropoxyethoxyethyl), sulfatoalkyl groups (e.g., 2-sulfatoethyl, 3-sulfatopropyl, 4-sulfatobutyl), hetero ring-substituted alkyl groups (e.g., 2-(pyrrolidine-2-one-1-yl) ethyl, tetrahydrofurfuryl), alkylsulfonylcarbamoylalkyl groups (e.g., methanesulfonylcarbamoylmethyl), acylcarbamoylalkyl groups (e.g., acetylcarbamoylmethyl), acylsulfamoylalkyl groups (e.g., acetylsulfamoylmethyl), alkylsulfonylsulfamoylalkyl groups (e.g., methanesulfonylsulfamoylmethyl) and halogen-substituted alkyl groups (e.g., 2-chloroethyl, 2,2,2-trifluoroethyl))], an alkenyl group (preferably including $C_{2-20}$ alkenyl groups, such as vinyl, allyl, 3-butenyl and oleyl, and alkenyl groups substituted with W as described above, such as sulfoalkenyl groups (e.g., 3-sulfo-2-propenyl)), an aryl group [including $C_{6-20}$, preferably $C_{6-10}$, particularly preferably $C_{6-8}$, unsubstituted or substituted aryl groups (e.g., aryl groups substituted with W as described above), such as phenyl, 1-naphthyl, 2-naphthyl, p-methoxyphenyl, p-methylphenyl and p-chlorophenyl], or an heterocyclic group [including $C_{1-20}$, preferably $C_{3-10}$, particularly preferably $C_{4-8}$, unsubstituted or substituted heterocyclic groups (e.g., heterocyclic groups substituted with W as described above), such as 2-furyl, 2-thienyl, 2-pyridyl, 3-pyrazolyl, 3-isooxazolyl, 3-isothiazolyl, 2-imidazolyl, 2-oxazolyl, 2-thiazolyl, 2-pyridazyl, 2-pyrimidyl, 3-pyrazyl, 2-(1,3,5-triazolyl), 3-(1,2,4-triazolyl), 5-tetrazolyl, 5-methyl-2-thienyl and 4-methoxy-2-pyridyl].

As $Ra_1$ and $Ra_2$ each, a hydrogen atom, an alkyl group or a sulfoalkyl group, especially an alkyl or sulfoalkyl group, are preferred.

Each of $Ma_1$ to $Ma_7$ represents a methine group, which may have a substituent. Such a substituent may be any of the foregoing substituent group W. Suitable examples of a substituent the methine group include $C_{1-20}$ alkyl groups (e.g., methyl, ethyl, i-propyl), halogen atoms (e.g., chlorine, bromine, iodine, fluorine), a nitro group, $C_{1-20}$ alkoxy groups (e.g., methoxy, ethoxy), $C_{6-26}$ aryl groups (e.g., phenyl, 2-naphthyl), $C_{0-20}$ heterocyclic groups (e.g., 2-pyridyl, 3-pyridyl), $C_{6-20}$ aryloxy groups (e.g., phenoxy, 1-naphthoxy, 2-naphthoxy), $C_{1-20}$ acylamino groups (e.g., acetylamino, benzoylamino), $C_{1-20}$ carbamoyl groups (e.g., N,N-dimethylcarbamoyl), a sulfo group, a hydroxyl group, a carboxyl group, $C_{1-20}$ alkylthio groups (e.g., methylthio), and a cyano group. Also, each methine group can form a ring by combining with another methine group or an auxochrome. Preferably, $Ma_1$ to $Ma_7$ are each an unsubstituted, ethyl-substituted or methyl-substituted methine group.

$na^1$ and $na^2$ are each 0 or 1, preferably 0. $Ka^1$ is an integer of 0 to 3, preferably an integer of 0 to 2, particularly preferably 0 or 1. When $ka^1$ is 2 or 3, two or three ($Ma_3=Ma_4$)s may be the same or different.

$Cl_6$ represents an ion for neutralization of electric charge, and y6 represents a number of ions required for neutralization of electric charges. Additionally, the chromophore of formula (8) may be linked with a linkage group $L_1$ at any site thereof.

The chromophores preferred as merocyanine chromophores are represented by the following formula (9):

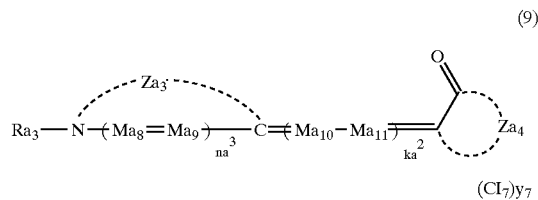

(9)

(Cl₇)y₇ wherein $Za_3$ represents atoms forming a 5- or 6-membered nitrogen containing hetero ring, which may be condensed with a benzene ring, a benzofuran ring, a pyridine ring, a pyrrole ring, an indole ring or a thiophene ring; $Za_4$ represents atoms forming an acid nucleus; $Ra_3$ represent a hydrogen atom, an alkyl group, an alkenyl group, an aryl group or a heterocyclic group (preferred examples of which are the same as those of $Ra_1$ and $Ra_2$ each); each of $Ma_8$ to $Ma_{11}$ represents a methine group (preferred examples of which are the same as those of $Ma_1$ to $Ma_7$); $na^3$ is 0 or 1; and $ka^2$ is an integer of 0 to 3, preferably an integer of 0 to 2, particularly preferably 1 or 2.

When $ka^2$ is 2 or 3, ($Ma_{10}$-$Ma_{11}$)s maybe the same or different.

$Cl_7$ represents an ion for neutralization of electric charge, and y7 represents a number of ions required for neutralization of electric charges. Additionally, when Dye2 represents a chromophore other than oxabarbituric dimethinemerocyanine, the chromophore of formula (9) may be linked with a linkage group $L_1$ at any site thereof. On the other hand, when Dye2 represents oxabarbituric dimetnine merocyanine, the substituent on the barbituric acid is required to link with $L_1$ for reasons of orientation control of the second layer.

The term "oxabarbituric dimethinemercocyanine" used herein refers to the structure represented by formula (7) when $Za_3$ constitutes oxazole, $Za_4$ constitutes barbituric acid and $ka^2$ represents 1 in formula (9).

The chromophores preferred as oxonol chromophores are represented by the following formula (10):

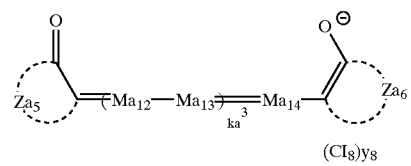

(10)

(Cl₈)y₈ wherein $Za_5$ and $Za_6$ each represent atoms constituting an acid nucleus, $Ma_{12}$ to $Ma_{14}$ each represent a methine group (suitable examples of which are the same as those of $Ma_1$ to $Ma_7$), and $ka^3$ is an integer of 0 to 3. When $ka^2$ is 2 or 3, ($Ma_{12}$-$Ma_{13}$)s may be the same or different.

And $Cl_8$ represents an ion for neutralization of electric charge, and y8 represents a number of ions required for neutralization of electric charges. Additionally, the oxonol chromophore may be linked with a linkage group $L_1$ at any site thereof.

Examples of a hetero ring constituted of $Za_1$, $Za_2$ and $Za_3$ each include $C_{3-25}$ oxazole nuclei [including oxazole nuclei (e.g., 2-3-methyloxazolyl, 2-3-ethyloxazolyl, 2-3,4-diethyloxazolyl), benzoxazolyl nuclei (e.g., 2-3-methylbenzoxazolyl, 2-3-ethylbezoxazolyl, 2-3-sulfoethylbenzoxazolyl, 2-3-sulfopropylbenzoxazolyl, 2-3-methylethylbenzoxazolyl, 2-3-methoxyethylbenzoxazolyl, 2-3-sulfobutylbenzoxazolyl, 2-3-(3-naphthoxyethyl) benzoxazolyl, 2-3,5-dimethylbenzoxazolyl, 2-6-chloro-3-methylbenzoxazolyl, 2-5-bromo-3-methylbenzoxazolyl, 2-3-ethyl-5-methoxybenzoxazolyl, 2-5-phenyl-3-sulfopropylbenzoxazolyl, 2-5-(4-bromophenyl)-3-sulfobutylbenzoxazolyl, 2-3-dimethyl-5,6-dimethylthiobenzoxazolyl), naphthoxazolyl nuclei (e.g., 2-3-methyl-β-naphthoxazolyl, 2-3-methyl-α-naphthoxazolyl, 2-3-sulfopropyl-β-naphthoxazolyl, 2-3-sulfopropyl-γ-naphthoxazolyl)], 3-25C thiazole nuclei (e.g., 2-3-methylthiazolyl, 2-3-ethylthiazolyl, 2-3-sulfopropylthiazolyl, 2-3-sulfobutylthiazolyl, 2-3,4-dimethylthiazolyl, 2-3,4,4-trimethylthiazolyl, 2-3-carboxyethylthiazolyl, 2-3-methylbenzothiazolyl, 2-3-ethylbenzothiazolyl, 2-3-butylbenzothiazolyl, 2-3-sulfopropylbenzothiazolyl, 2-3-sulfobutylbenzothiazolyl, 2-3-methyl-β-naphthothiazolyl, 2-3-sulfopropyl-γ-naphthothiazolyl, 2-3-(1-naphthoxyethyl)benzothiazolyl, 2-3,5-dimethylbenzothiazolyl, 2-6-chloro-3-methylbenzothiazolyl, 2-6-iodo-3-ethylbenzothiazolyl, 2-5-bromo-3-methylbenzothiazolyl, 2-3-ethyl-5-methoxybenzothiazolyl, 2-5-phenyl-3-sulfopropylbenzothiazolyl, 2-5-(4-bromophenyl)3-sulfobutylbenzothiazolyl, 2-3-dimethyl-5,6-dimethylthiobenzothiazolyl), $C_{3-25}$ imidazole nuclei (e.g., 2-1,3-diethylimidazolyl, 2-1,3-dimethylimidazolyl, 2-1-methylbenzimidazolyl, 2-1,3,4-triethylimidazolyl, 2-1,3-diethylbenzimidazolyl, 2-1,3,5-trimethylbenzimidazolyl, 2-6-chloro-1,3-dimethylbenzimidazolyl, 2-5,6-dichloro-1,3-diethylbenzimidazolyl, 2-1,3-disulfopropyl-5-cyano-6-chlorobenzimidazolyl), $C_{10-30}$ indolenine nuclei (e.g., 3,3-dimethylindolene), $C_{9-25}$ quinoline nuclei (e.g., 2-1-methylquinolyl, 2-1-ethylquinolyl, 2-1-methyl-6-chloroquinolyl, 2-1,3-diethylquinolyl, 2-1-methyl6-methylquinolyl, 2-1-sulfopropylquinolyl, 4-1-methylquinolyl, 4-1-sulfoethylquinolyl, 4-1-methyl-7-chloroquinolyl, 4-1,8-diethylquinolyl, 4-1-methyl-6-methylthioquinolyl, 4-1-sulfopropylquinolyl), $C_{3-25}$ selenazole nuclei (e.g., 2-3-methylbenzoselenazolyl), and $C_{5-25}$ pyridine nuclei (e.g., 2-pyridyl). In addition to these nuclei, thiazoline nuclei, oxazoline nuclei, selenazoline nuclei, tellurazoline nuclei, tellurazole nuclei, benzotellurazole nuclei, imidazoline nuclei, imidazo[4,5-quinoxaline] nuclei, oxadiazole nuclei, thiadiazole nuclei, tetrazole nuclei and pyrimidine nuclei can be suitable for $Za_1$, $Za_2$ and $Za_3$ each.

Each of the rings described above may further have at least one substituent. Examples of such a substituent include the substituent group W described above. Preferably, alkyl groups (e.g., methyl, ethyl, propyl), halogen atoms (e.g., chlorine, bromine, iodine, fluorine), a nitro group, alkoxy groups (e.g., methoxy, ethoxy), aryl groups (e.g., phenyl), heterocyclic groups (e.g., 2-pyridyl, 3-pyridyl, 1-pyrrolyl, 2-thienyl), aryloxy groups (e.g., phenoxy), acylamino groups (e.g., acetylamino, benzoylamino), carbamoyl groups (e.g., N,N-dimethylcarbamoyl), a sulfo group, sulfonamido groups (e.g., methanesulfonamido), sulfamoyl groups (e.g., N-methylsulfamoyl), a hydroxyl group, a carboxyl group, alkylthio groups (e.g., methylthio) and a cyano group can be substituted on the hetero rings described above.

Of the hetero rings as described above, oxazole nuclei, imidazole nuclei and thiazole nuclei are preferred over the others. These hetero rings each may further be condensed with other rings. Examples of rings capable of condensing with those hetero rings include benzene rings, benzofuran rings, pyridine rings, pyrrole rings, indole rings and thiophene rings.

In particular, benzoxazole nuclei are preferred as $Za_1$, $Za_2$ and $Za_3$ each.

$Za_4$, $Za_5$ and $Za_6$ each represent atoms required for forming an acid nucleus, and such acid nuclei are defined in *The Theory of The Photographic Process*, 4th Edition (edited by T. H. James), page 198, Macmillan, (1977). Specifically, examples of such acid nuclei include 2-pyrazolone-5-one, pyrazolidine-3,5-dione, imidazoline-5-one, hydantoin, 2- or 4-thiohydantoin, 2-iminoxazolidine-4-one, 2-oxazoline-5-one, 2-thioxazoline-2,4-dione, isorhodanine, rhodanine, indane-1,3-dione, thiophene-3-one, thiophene-3-one-1,1-dioxide, indoline-2-one, indoline-3-one, 2-oxoindazolium, 5,7-dioxo-6,7-dihydrothiazolo[3,2-a]pyrimidine, 3,4-dihydroisoquinoline-4-one, 1,3-dioxane-4,6-dione, barbituric acid, 2-thiobarbituric acid, coumarin-2,4-dione, indazoline-2-one, pyrido[1,2-a]pyrimidine-1,3-dione, pyrazolo[1,5-b]quinazoline, and pyrazolopyridone.

Of these acid nuclei, hydantoin, rhodanine, barbituric acid and 2-oxazoline-5-one are preferred over the others. As to Za, barbituric acid is preferred in particular.

Examples of cyanine chromophores, merocyanine chromophores and oxonol chromophores include those described in F. M. Harmer, *Heterocyclic Compounds—Cyanine Dyes and Related Compounds*, John Wiley & Sons, New York, London (1964).

General formulae of preferable dyes include those disclosed in U.S. Pat. No. 5,994,051, pages 32 to 36, and U.S. Pat. No. 5,747,236, pages 39 to 34. And general formulae of preferable cyanine dyes, merocyanine dyes and rhodacyanine dyes include formulae (XI), (XII) and (XIII) illustrated in U.S. Pat. No. 5,340,694, columns 21 and 22 (provided that the numbers n12, n15, n17 and n18 have no limitations so long as they are integers of 0 or above, preferably 4 or below).

L1 represents a linkage group of formula (2) illustrated hereinbefore.

$A_1$, $A_2$, $A_3$ and $A_4$ each represent a carbonyl group or a sulfo group.

$Y_1$, $Y_2$ and $Y_3$ each represent a divalent group of formula —O—, —S— or —$NR_1$—, and $R_1$ represents a hydrogen atom, an alkyl group, an alkenyl group, an aryl group or a heterocyclic group. What are preferred as $R_1$ include those described as examples of $Ra_1$ and $Ra_2$.

$Y_4$ represents —NH—, —$NH_2^+$—, —S— or —O—, preferably —NH—, —$NH_2^+$— or —O—, particularly preferably —NH— or —$NH_2^+$—.

$Y_5$ and $Y_6$ each represent a hydroxyl group, a halogen atom, an alkoxy group, an aryloxy group, an acyloxy group, a heterocyclyloxy group, an alkyl- or aryloxycarbonyloxy group, an imidyloxycarbonyloxy group, an alkyl- or arylsulfonyl group or a heterocyclic group. More specifically, $Y_5$ and $Y_6$ include a hydroxyl group, halogen atoms (e.g., fluorine, chlorine, bromine, iodine), heterocyclic groups (or monovalent groups which are each formed by removing one hydrogen atom from NH group present in each of 5- or 6-membered, substituted or unsubstituted, aromatic or non-aromatic nitrogen-containing heterocyclic compounds, such as 1-imidazolyl group), alkoxy groups (preferably $C_{1-30}$ substituted or unsubstituted alkoxy groups, such as methoxy, ethoxy, isopropoxy, t-butoxy, n-octyloxy and 2-methoxyethoxy), aryloxy groups (preferably $C_{6-30}$ substituted or unsubstituted aryloxy groups, such as 4-nitrophenoxy and 2,4-dinitorphenoxy), heterocyclyloxy groups (preferably $C_{2-30}$ substituted or unsubstituted heterocyclyloxy groups, such as 1-phenyltetrazole-5-oxy, 2-tetrahydropyranyloxy and benzotriazole-1-ylxoy), acyloxy groups (preferably a formyloxy group, $C_{2-30}$ substituted or unsubstituted alkylcarbonyloxy groups and $C_{6-30}$ substituted or unsubstituted arylcarbonyloxy groups, such as formyloxy, acetyloxy, pivaloyloxy, stearoyloxy, benzoyloxy and p-methoxyphenylcarbonyloxy), alkoxycarbonyloxy groups (preferably $C_{2-30}$ substituted or unsubstituted alkoxyvarbonyloxy groups, such as methoxycarbonyloxy, ethoxycarbonyloxy, t-butoxycarbonyloxy and n-octylcarbonyloxy), aryloxycarbonyloxy groups (preferably $C_{7-30}$ substituted or unsubstituted aryloxycarbonyloxy groups, such as phenoxycarbonyloxy, p-methoxyphenoxycarbonyloxy and p-n-hexadecyloxyphenoxycarbonyloxy), alkyl- and arylsulfonyl groups (preferably $C_{1-30}$ substituted or unsubstituted alkylsulfonyl groups and $C_{6-30}$ substituted or unsubstituted arylsulfonyl groups, such as methylsulfonyl, ethylsulfonyl, phenylsulfonyl and p-methylphenylsulfonyl), and imidyloxycarbonyloxy groups (e.g., succinimidyloxycarbonyloxy).

The groups preferred as $Y_5$ and $Y_6$ are hydroxyl, chloro, bromo, methoxy, ethoxy, p-nitrophenyl, acetyloxy, methanesulfonyloxy, succinimidyloxycarbonyloxy and 1-imidazolyl groups. In particular, a hydroxyl group is suitable for $Y_5$ and $Y_6$ each.

$G_1$ to $G_6$ represent divalent linkage groups, which may be any of known ones. Preferably, they each represent an alkylene group (preferably an alkylene group containing 1 to 20 carbon atoms, which is hereinafter abbreviated as a $C_{1-20}$ alkylene group, with examples including methylene, ethylene, propylene, butylene, pentylene, hexylene and octylene), an arylene group (preferably a $C_{6-26}$ arylene group, such as phenylene or naphthylene), an alkenylene group (preferably a $C_{2-20}$ alkenylene group, such as ethenylene or propenylene), an alkynylene group (preferably $C_{2-20}$ alkynylene group, such as ethynylene or propynylene), an amido group, an ester group, a sulfoamido group, a sulfonate group, an uredio group, a sulfonyl group, a sulfinyl group, a thioether group, an ether group, a carbonyl group, —$NR_{51}$— (wherein $R_{51}$ represents a hydrogen atom or a monovalent substituent, suitable examples of which include the substituent group W), a heterylene group (preferably a $C_{1-26}$ heterylene group, such as 6-chloro-1,3,5-triazyl-2,4-diyl, pyrimidine-2,4-diyl or quinoxaline-2,3-diyl), or a $C_{0-100}$, preferably $C_{1-20}$, linkage group formed by combining at least two of the above-described groups.

The groups far preferred as $G_1$ to $G_6$ are alkylene groups (preferably containing 1 to 20 carbon atoms, such as methylene, ethylene, propylene, butylene, hexylene, octylene, 2-methylbutylene and 3-phenylpentylene), alkenylene groups (preferably containing 2 to 20 carbon atoms, such as ethenylene, propenylene and 2-butenylene), or arylene groups (preferably containing 6–26 carbon atoms, such as 1,4-phenylene and 1,4-naphthylene). These groups each may be substituted with any of the substituent group W. In particular, alkylene groups, especially linear, unsubstituted $C_{1-8}$ alkylene groups, are preferred over the others.

P represents a protective group. The protective group represented by P may be any of those described as the protective groups for hydroxyl and amino groups in Theodora W. Greene and Peter G. M. Wuts, *Protective Groups in Organic Synthesis*, 3rd edition, John Wiley & Sons, New York, London. However, it is preferable that the protective group as P be stable under basic conditions but lose its protective function under acidic conditions.

Suitable examples of a protective group of hydroxyl group include methoxymethyl, 2-methoxyethoxymethyl, tetrahydropyranyl, t-butyl, benzyl, trimethylsilyl and t-butyldimethylsilyl groups.

Suitable examples of a protective group of amino group include t-butoxycarbonyl, benzyloxycarbonyl, benzyl, triphenylmethyl, benzylidene, benzensulfenyl, pivaloyloxymethyl and phthalimido groups.

Protective groups preferred as P are 2-methoxyethoxymethyl, tetrahydropyranyl, t-butyl, benzyl, t-butoxycarbonyl, benzyloxycarbonyl, triphenylmethyl, benzylidine and phthalimido groups. Of these groups, t-butoxycarbonyl, triphenylmethyl and benzylidene groups are more preferred as P.

$CI_1$ to $CI_8$ each represent an ion for neutralization of electric charge. Whether a certain compound is a cation or an anion or has net ionic charge depends on what kinds of substituents it has. Typical cations are ammonium ions and alkali metal ions, while anions may be any of inorganic ions or organic ions.

Examples of such a cation include sodium ion, potassium ion, triethylammonium ion, diethyl(i-propyl) ammonium ion, pyridinium ion and 1-ethylpyridinium ion, and examples of such an anion include halide ions (e.g., chloride ion, bromide ion, fluoride ion, iodide ion), substituted arylsulfonate ions (e.g., paratoluenesulfonate ion), alkylsulfate ions (e.g., methylsulfate ion), sulfate ion, perchlorate ion, tetrafluoroborate ion and acetate ion. y1 to y8 each represent a number of ions required for neutralization of electric charges.

Suitable examples of present compounds represented by formula (1) are shown below. However, these examples should not be construed as limiting the scope of the present invention. Additionally, the structural formulae of the present compounds as shown below are each no more than one extreme structure among many resonance structures each of the present compounds can take, and so each compound may take another resonance structure.

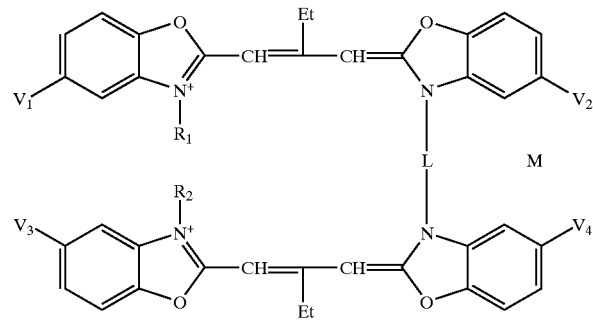

| No. | $R_1$ | $R_2$ | $V_1$ | $V_2$ | $V_3$ | $V_4$ | L* | M |
|---|---|---|---|---|---|---|---|---|
| 1 | Et | $(CH_2)_3SO_3^-$ | $SO_3^-$ | $SO_3^-$ | Cl | Ph | $-(CH_2)_3CONH(CH_2)_2NHCO(CH_2)_3-$ | $Na^+$ |
| 2 | Et | $(CH_2)_3SO_3^-$ | $SO_3^-$ | $SO_3^-$ | Cl | Ph | $-(CH_2)_3CONH(CH_2)_3NHCO(CH_2)_3-$ | $Na^+$ |
| 3 | Et | $(CH_2)_3SO_3^-$ | $SO_3^-$ | $SO_3^-$ | Cl | Ph | $-(CH_2)_3CONH(CH_2)_4NHCO(CH_2)_3-$ | $Na^+$ |
| 4 | Et | $(CH_2)_3SO_3^-$ | $SO_3^-$ | $SO_3^-$ | Ph | Cl | $-(CH_2)_3CONH(CH_2)_2NHCOCH_2-$ | $Na^+$ |
| 5 | Et | $(CH_2)_3SO_3^-$ | $SO_3^-$ | $SO_3^-$ | Ph | Ph | $-(CH_2)_3CONH(CH_2)_2NHCO(CH_2)_3-$ | $Na^+$ |
| 6 | $(CH_2)_3SO_3^-$ | $(CH_2)_3SO_3^-$ | $SO_3^-$ | Cl | Br | Ph | $-(CH_2)_3CONH(CH_2)_2NHCO(CH_2)_3-$ | $Na^+$ |
| 7 | $(CH_2)_3SO_3^-$ | $(CH_2)_3SO_3^-$ | $SO_3^-$ | Cl | thienyl | Br | $-(CH_2)_3CONH(CH_2)_2NHCO(CH_2)_3-$ | $Na^+$ |
| 8 | $(CH_2)_4SO_3^-$ | $(CH_2)_3SO_3^-$ | $SO_3^-$ | $SO_3^-$ | Br | Br | $-(CH_2)_3CONH(CH_2)_2NHCO(CH_2)_3-$ | $2Na^+$ |
| 9 | Et | $(CH_2)_3SO_3^-$ | $SO_3^-$ | $SO_3^-$ | 4,5benzo | Br | $-(CH_2)_3CONH(CH_2)_2NHCOCH_2-$ | $Na^+$ |
| 10 | Et | $(CH_2)_3SO_3^-$ | $SO_3^-$ | $SO_3^-$ | 5,6benzo | Ph | $-(CH_2)_3CONH(CH_2)_2NHCO(CH_2)_3-$ | $Na^+$ |

*L links with the upper dye moiety on the left side thereof.

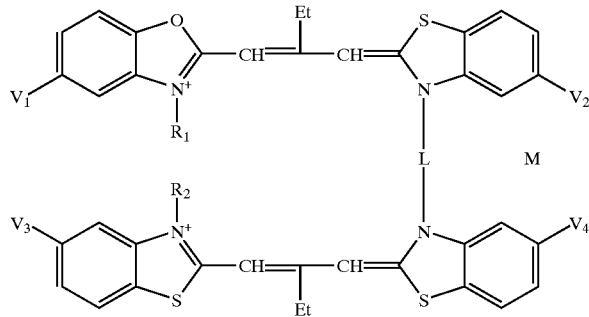

| No. | $R_1$ | $R_2$ | $V_1$ | $V_2$ | $V_3$ | $V_4$ | L* | M |
|---|---|---|---|---|---|---|---|---|
| 21 | Et | $(CH_2)_3SO_3^-$ | $SO_3^-$ | $SO_3^-$ | Cl | Ph | —$(CH_2)_3CONH(CH_2)_2NHCO(CH_2)_3$— | $Na^+$ |
| 22 | Et | $(CH_2)_3SO_3^-$ | $SO_3^-$ | $SO_3^-$ | Cl | Ph | —$(CH_2)_3CONH(CH_2)_3NHCO(CH_2)_3$— | $Na^+$ |
| 23 | Et | $(CH_2)_3SO_3^-$ | $SO_3^-$ | $SO_3^-$ | Cl | Ph | —$(CH_2)_3CONH(CH_2)_4NHCO(CH_2)_3$— | $Na^+$ |
| 24 | Et | $(CH_2)_3SO_3^-$ | $SO_3^-$ | $SO_3^-$ | Ph | Cl | —$(CH_2)_3CONH(CH_2)_2NHCOCH_2$— | $Na^+$ |
| 25 | Et | $(CH_2)_3SO_3^-$ | $SO_3^-$ | $SO_3^-$ | Ph | Ph | —$(CH_2)_3CONH(CH_2)_2NHCO(CH_2)_3$— | $Na^+$ |
| 26 | $(CH_2)_3SO_3^-$ | $(CH_2)_3SO_3^-$ | $SO_3^-$ | Cl | Br | Ph | —$(CH_2)_3CONH(CH_2)_2NHCO(CH_2)_3$— | $Na^+$ |
| 27 | $(CH_2)_3SO_3^-$ | $(CH_2)_3SO_3^-$ | $SO_3^-$ | Cl | thienyl | Br | —$(CH_2)_3CONH(CH_2)_2NHCO(CH_2)_3$— | $Na^+$ |
| 28 | $(CH_2)_4SO_3^-$ | $(CH_2)_3SO_3^-$ | $SO_3^-$ | $SO_3^-$ | Br | Br | —$(CH_2)_3CONH(CH_2)_2NHCO(CH_2)_3$— | $2Na^+$ |
| 29 | Et | $(CH_2)_3SO_3^-$ | $SO_3^-$ | $SO_3^-$ | 4,5benzo | Br | —$(CH_2)_3CONH(CH_2)_2NHCOCH_2$— | $Na^+$ |
| 30 | Et | $(CH_2)_3SO_3^-$ | $SO_3^-$ | $SO_3^-$ | 5,6benzo | Ph | —$(CH_2)_3CONH(CH_2)_2NHCO(CH_2)_3$— | $Na^+$ |

*L links with the upper dye moiety on the left side thereof.

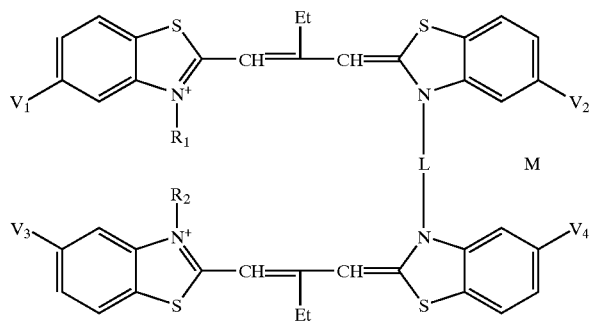

| No. | $R_1$ | $R_2$ | $V_1$ | $V_2$ | $V_3$ | $V_4$ | L* | M |
|---|---|---|---|---|---|---|---|---|
| 31 | Et | $(CH_2)_3SO_3^-$ | $SO_3^-$ | $SO_3^-$ | Cl | Ph | —$(CH_2)_3CONH(CH_2)_2NHCO(CH_2)_3$— | $Na^+$ |
| 32 | Et | $(CH_2)_3SO_3^-$ | $SO_3^-$ | $SO_3^-$ | Cl | Ph | —$(CH_2)_3CONH(CH_2)_3NHCO(CH_2)_3$— | $Na^+$ |
| 33 | Et | $(CH_2)_3SO_3^-$ | $SO_3^-$ | $SO_3^-$ | Cl | Ph | —$(CH_2)_3CONH(CH_2)_4NHCO(CH_2)_3$— | $Na^+$ |
| 34 | Et | $(CH_2)_3SO_3^-$ | $SO_3^-$ | $SO_3^-$ | Ph | Cl | —$(CH_2)_3CONH(CH_2)_2NHCOCH_2$— | $Na^+$ |
| 35 | Et | $(CH_2)_3SO_3^-$ | $SO_3^-$ | $SO_3^-$ | Ph | Ph | —$(CH_2)_3CONH(CH_2)_2NHCO(CH_2)_3$— | $Na^+$ |
| 36 | $(CH_2)_3SO_3^-$ | $(CH_2)_3SO_3^-$ | $SO_3^-$ | Cl | Br | Ph | —$(CH_2)_3CONH(CH_2)_2NHCO(CH_2)_3$— | $Na^+$ |
| 37 | $(CH_2)_3SO_3^-$ | $(CH_2)_3SO_3^-$ | $SO_3^-$ | Cl | thienyl | Br | —$(CH_2)_3CONH(CH_2)_2NHCO(CH_2)_3$— | $Na^+$ |
| 38 | $(CH_2)_4SO_3^-$ | $(CH_2)_3SO_3^-$ | $SO_3^-$ | $SO_3^-$ | Br | Br | —$(CH_2)_3CONH(CH_2)_2NHCO(CH_2)_3$— | $2Na^+$ |
| 39 | Et | $(CH_2)_3SO_3^-$ | $SO_3^-$ | $SO_3^-$ | 4,5benzo | Br | —$(CH_2)_3CONH(CH_2)_2NHCOCH_2$— | $Na^+$ |
| 40 | Et | $(CH_2)_3SO_3^-$ | $SO_3^-$ | $SO_3^-$ | 5,6benzo | Ph | —$(CH_2)_3CONH(CH_2)_2NHCO(CH_2)_3$— | $Na^+$ |

*L links with the upper dye moiety on the left side thereof.

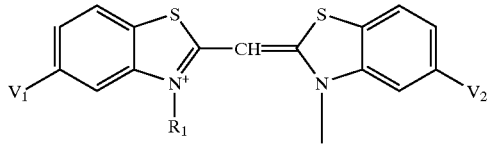

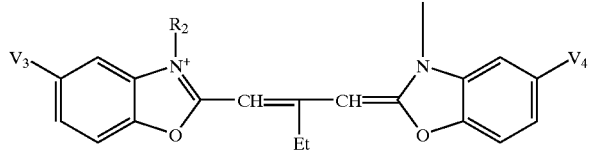

| No. | R₁ | R₂ | V₁ | V₂ | V₃ | V₄ | L* | M |
|---|---|---|---|---|---|---|---|---|
| 31 | Et | $(CH_2)_3SO_3^-$ | $SO_3^-$ | $SO_3^-$ | Cl | Ph | $-(CH_2)_3CONH(CH_2)_2NHCO(CH_2)_3-$ | Na⁺ |
| 32 | Et | $(CH_2)_3SO_3^-$ | $SO_3^-$ | $SO_3^-$ | Br | Ph | $-(CH_2)_3CONH(CH_2)_3NHCO(CH_2)_3-$ | Na⁺ |
| 33 | Et | $(CH_2)_3SO_3^-$ | $SO_3^-$ | $SO_3^-$ | Cl | Ph | $-(CH_2)_3CONH(CH_2)_4NHCO(CH_2)_3-$ | Na⁺ |
| 34 | Et | $(CH_2)_3SO_3^-$ | $SO_3^-$ | $SO_3^-$ | 4,5benzo | Cl | $-(CH_2)_3CONH(CH_2)_2NHCOCH_2-$ | Na⁺ |
| 35 | $(CH_2)_3SO_3^-$ | $(CH_2)_3SO_3^-$ | $SO_3^-$ | Cl | Ph | Ph | $-(CH_2)_3CONH(CH_2)_2NHCO(CH_2)_3-$ | Na⁺ |

*L links with the upper dye moiety on the left side thereof.

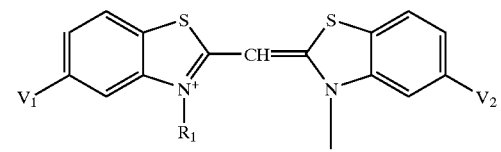

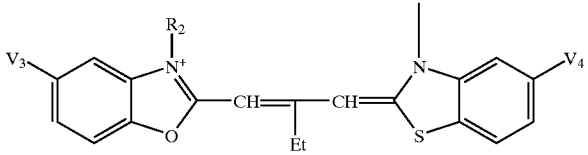

| No. | R₁ | R₂ | V₁ | V₂ | V₃ | V₄ | L* | M |
|---|---|---|---|---|---|---|---|---|
| 36 | $(CH_2)_3SO_3^-$ | $(CH_2)_3SO_3^-$ | $SO_3^-$ | Cl | Cl | Ph | $-(CH_2)_3CONH(CH_2)_2NHCO(CH_2)_3-$ | Na⁺ |
| 37 | $(CH_2)_3SO_3^-$ | $(CH_2)_3SO_3^-$ | $SO_3^-$ | Cl | thienyl | Br | $-(CH_2)_3CONH(CH_2)_3NHCO(CH_2)_3-$ | Na⁺ |
| 38 | $(CH_2)_4SO_3^-$ | $(CH_2)_3SO_3^-$ | $SO_3^-$ | $SO_3^-$ | Br | Br | $-(CH_2)_3CONH(CH_2)_4NHCO(CH_2)_3-$ | 2Na⁺ |
| 39 | Et | $(CH_2)_3SO_3^-$ | $SO_3^-$ | $SO_3^-$ | 4,5benzo | Cl | $-(CH_2)_3CONH(CH_2)_2NHCOCH_2-$ | Na⁺ |
| 40 | Et | $(CH_2)_3SO_3^-$ | $SO_3^-$ | $SO_3^-$ | 5,6benzo | Ph | $-(CH_2)_3CONH(CH_2)_2NHCO(CH_2)_3-$ | Na⁺ |

*L links with the upper dye moiety on the left side thereof.

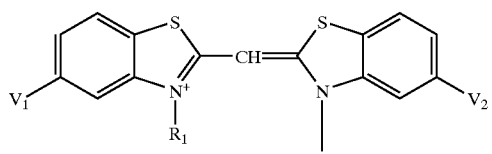

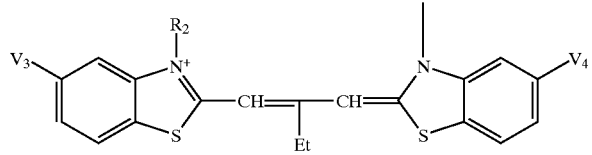

| No. | R₁ | R₂ | V₁ | V₂ | V₃ | V₄ | L* | M |
|---|---|---|---|---|---|---|---|---|
| 41 | Et | $(CH_2)_3SO_3^-$ | $SO_3^-$ | $SO_3^-$ | Cl | Ph | $-(CH_2)_3CONH(CH_2)_2NHCO(CH_2)_3-$ | Na⁺ |
| 42 | Et | $(CH_2)_3SO_3^-$ | $SO_3^-$ | $SO_3^-$ | Br | Ph | $-(CH_2)_3CONH(CH_2)_3NHCO(CH_2)_3-$ | Na⁺ |
| 43 | Et | $(CH_2)_3SO_3^-$ | $SO_3^-$ | $SO_3^-$ | Cl | Ph | $-(CH_2)_2O(CH_2)_2CONH-(CH_2)_4NHCO(CH_2)_3-$ | Na⁺ |

-continued

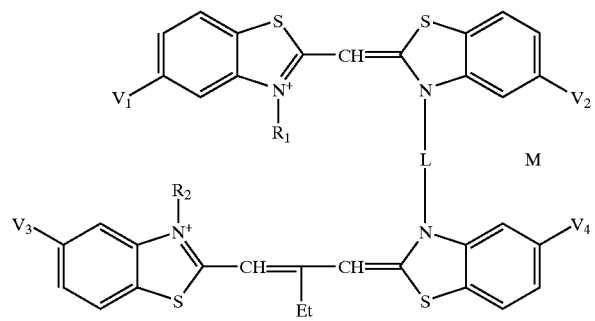

| No. | R₁ | R₂ | V₁ | V₂ | V₃ | V₄ | L* | M |
|---|---|---|---|---|---|---|---|---|
| 44 | Et | (CH₂)₃SO₃⁻ | SO₃⁻ | SO₃⁻ | 4,5benzo | Cl | —(CH₂)₃CONH(CH₂)₂NHCOCH₂— | Na⁺ |
| 45 | (CH₂)₃SO₃⁻ | (CH₂)₃SO₃⁻ | SO₃⁻ | Cl | Ph | Ph | —(CH₂)₃CONH(CH₂)₂O(CH₂)₂NHCO(CH₂)₅— | Na⁺ |

*L links with the upper dye moiety on the left side thereof.

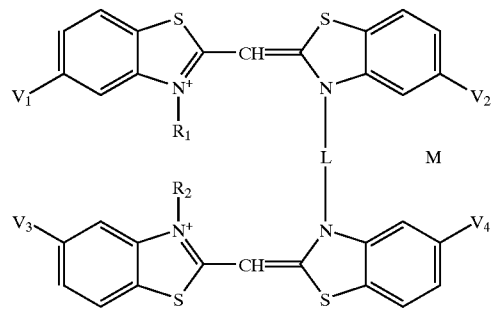

| No. | R₁ | R₂ | V₁ | V₂ | V₃ | V₄ | L* | M |
|---|---|---|---|---|---|---|---|---|
| 46 | (CH₂)₃SO₃⁻ | (CH₂)₃SO₃⁻ | SO₃⁻ | Cl | Cl | Ph | —(CH₂)₃CONH(CH₂)₂NHCO(CH₂)₃— | Na⁺ |
| 47 | (CH₂)₃SO₃⁻ | (CH₂)₃SO₃⁻ | SO₃⁻ | Cl | thienyl | Br | —(CH₂)₃CONH(CH₂)₂NHCO(CH₂)₃— | Na⁺ |
| 48 | (CH₂)₃SO₃⁻ | (CH₂)₃SO₃⁻ | SO₃⁻ | SO₃⁻ | Br | Br | —(CH₂)₃CONH(CH₂)₂NHCO(CH₂)₂O(CH₂)₂— | 2Na⁺ |
| 49 | Et | (CH₂)₃SO₃⁻ | SO₃⁻ | SO₃⁻ | 4,5benzo | Cl | —(CH₂)₃CONH(CH₂)₂NHCOCH₂— | Na⁺ |
| 50 | Et | (CH₂)₃SO₃⁻ | SO₃⁻ | SO₃⁻ | 5,6benzo | Ph | —(CH₂)₃CONH(CH₂)₂NHCO(CH₂)₃— | Na⁺ |

*L links with the upper dye moiety on the left side thereof.

No. 51

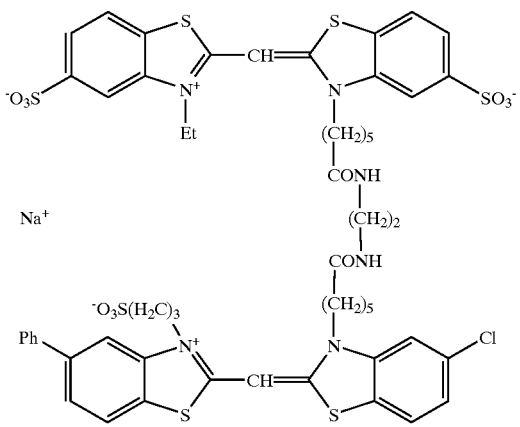

-continued
No. 52
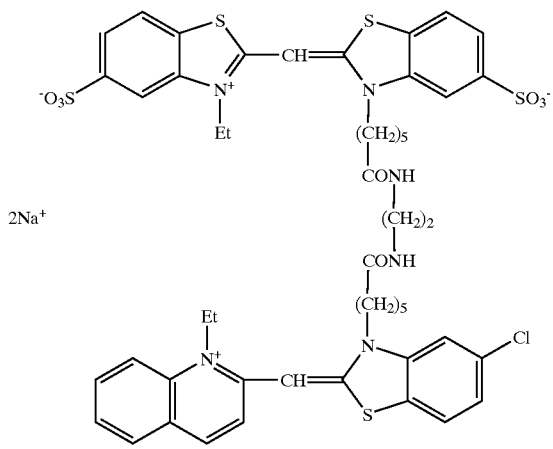
No. 53
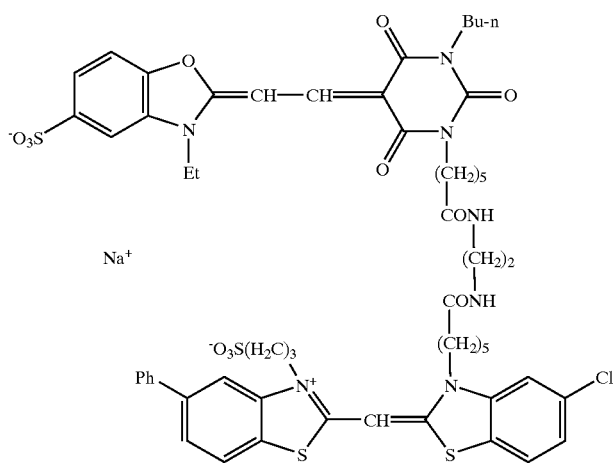
No. 54
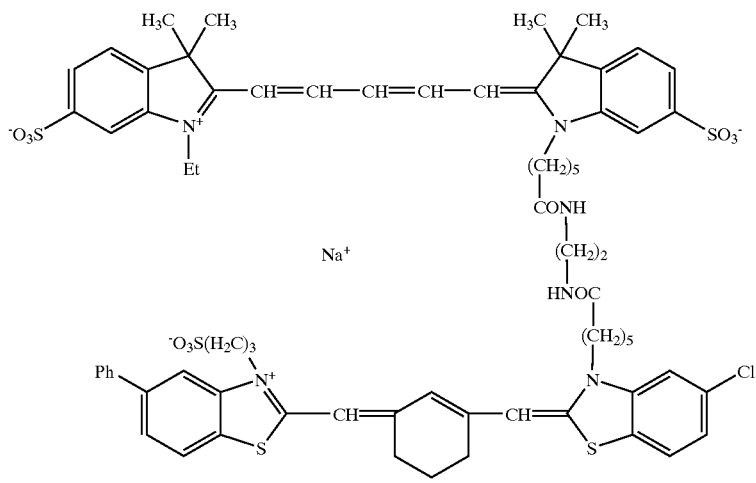

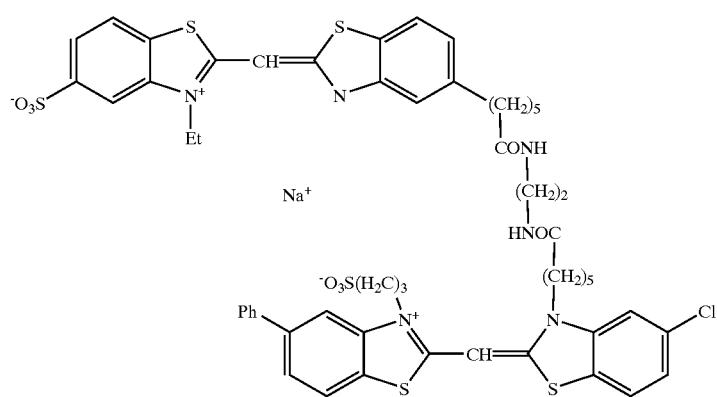

No. 55

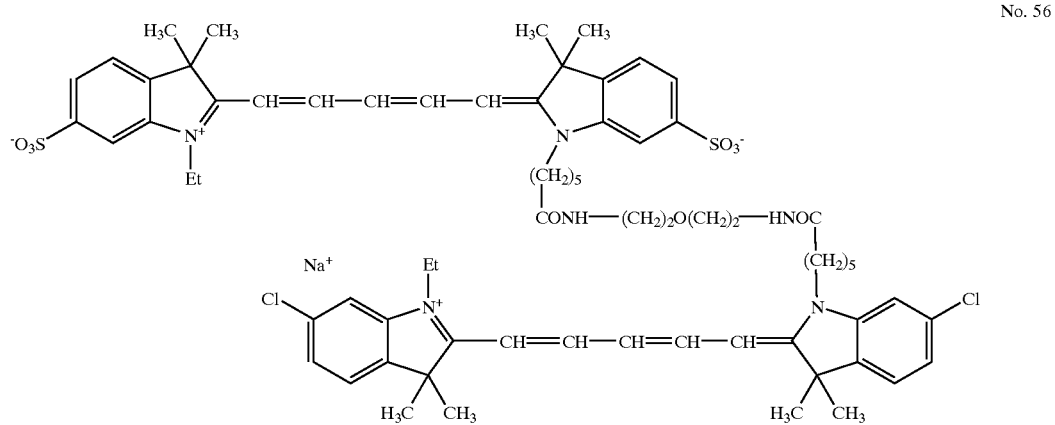

No. 56

Suitable examples of present compounds represented by formula (3) are shown below. However, these examples should not be construed as limiting the scope of the present invention. Additionally, the structural formulae of the present compounds as shown below are each no more than one extreme structure among many resonance structures each of the present compounds can take, and so each compound may take another resonance structure.

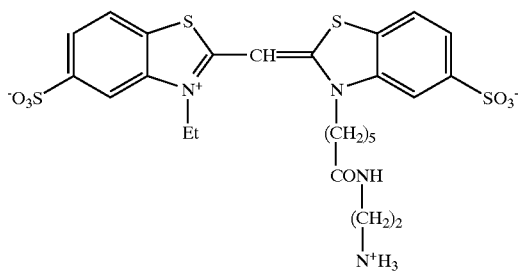

No. 57

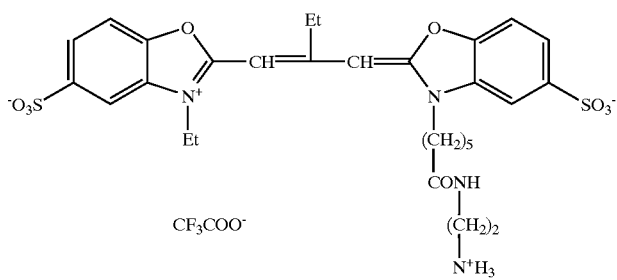

No. 58

No. 59
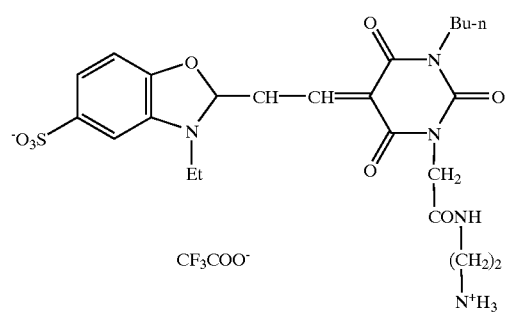
No. 60
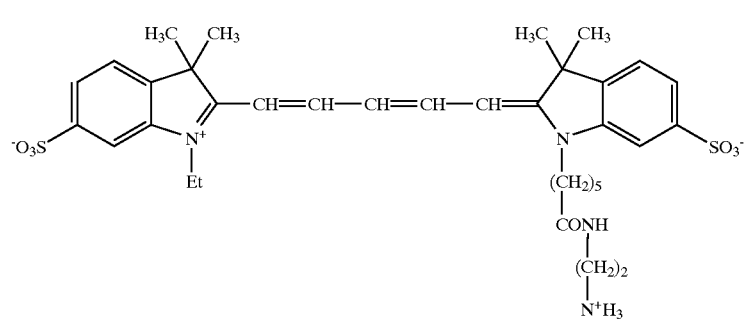
No. 61
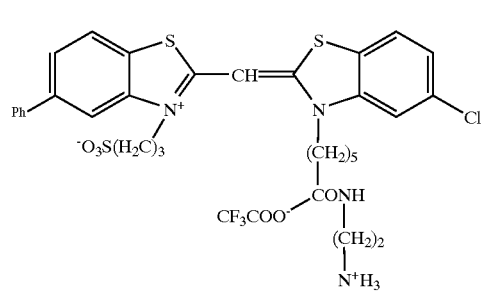
No. 62
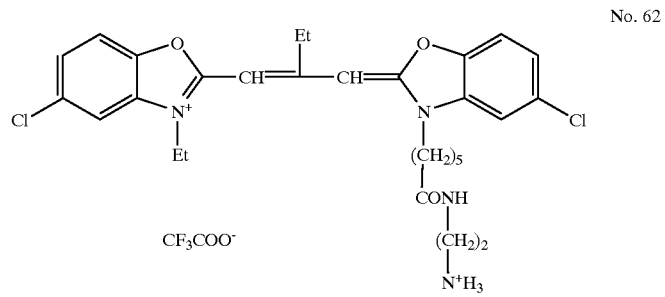
No. 63
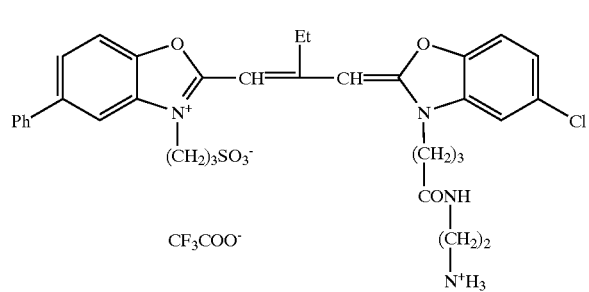

-continued
No. 64
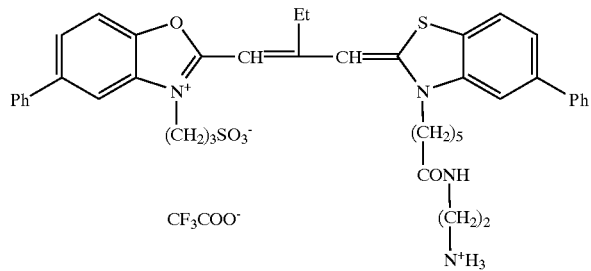
No. 65
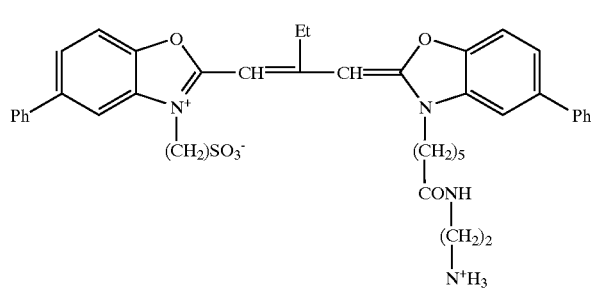
No. 66
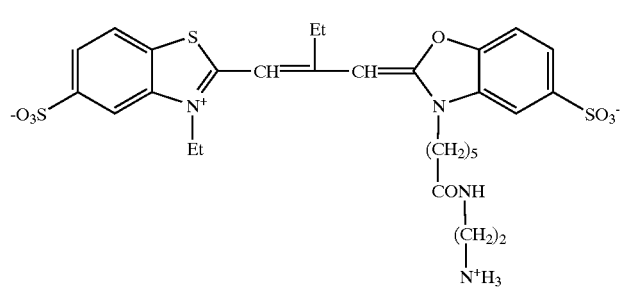
No. 67
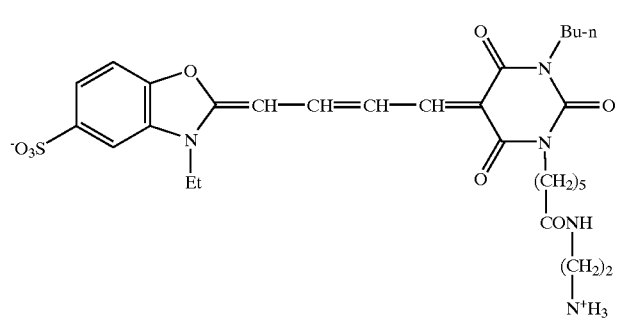
No. 68
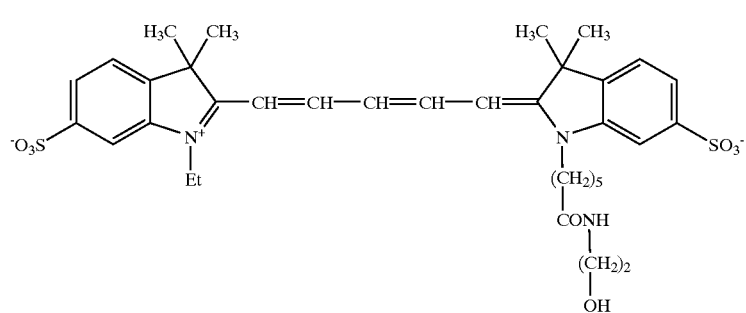

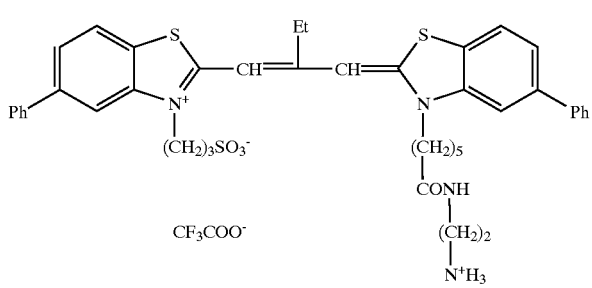

No. 69

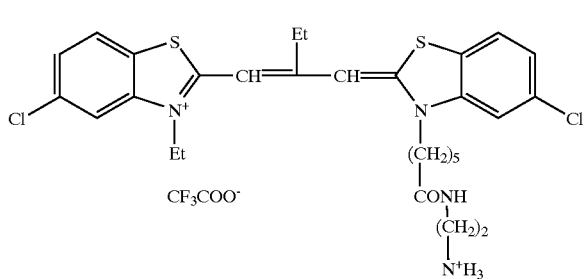

No. 70

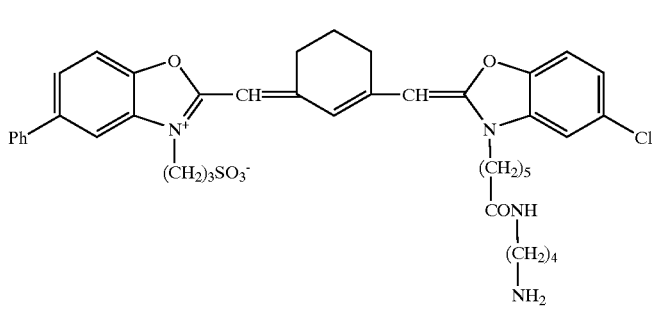

No. 71

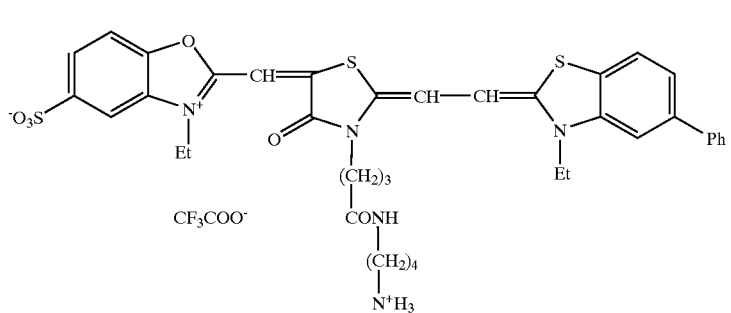

No. 72

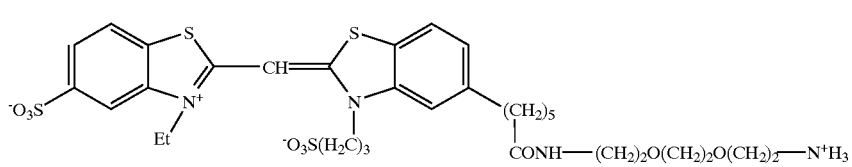

No. 73

Suitable examples of present compounds represented by formula (5) are shown below. However, these examples should not be construed as limiting the scope of the present invention. Additionally, the structural formulae of the present compounds as shown below are each no more than one extreme structure among many resonance structures each of the present compounds can take, and so each compound may take another resonance structure.

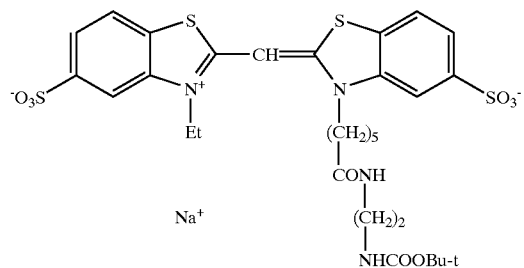
No. 74
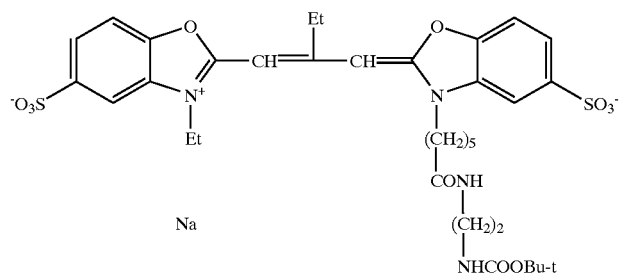
No. 75
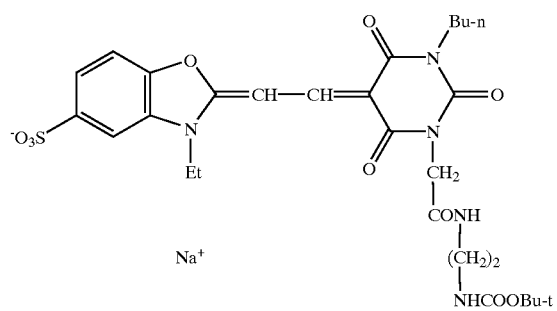
No. 76
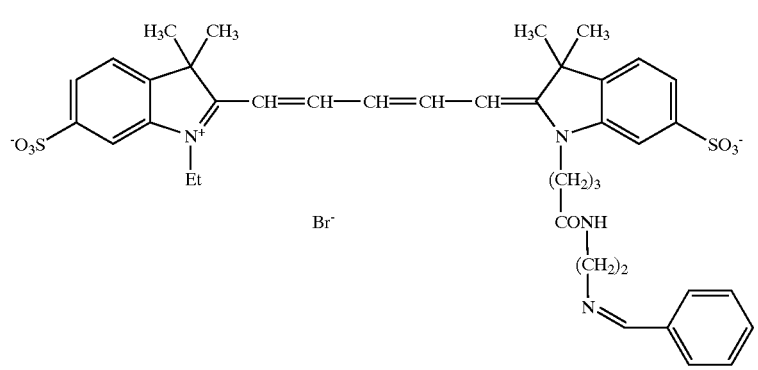
No. 77
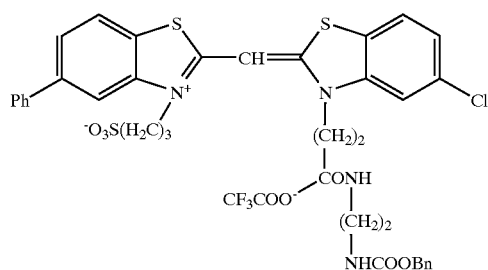
No. 78

-continued
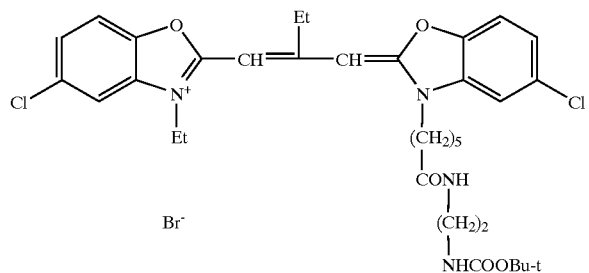
No. 79
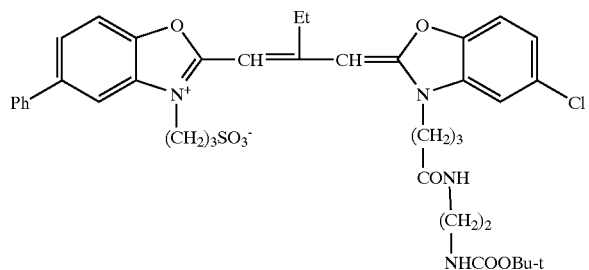
No. 80
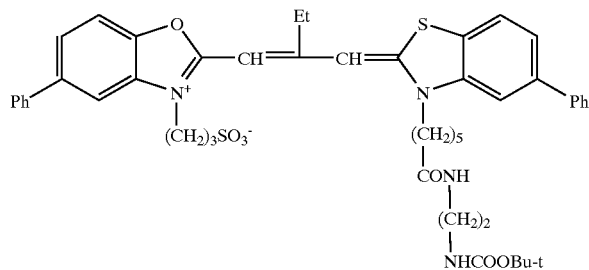
No. 81
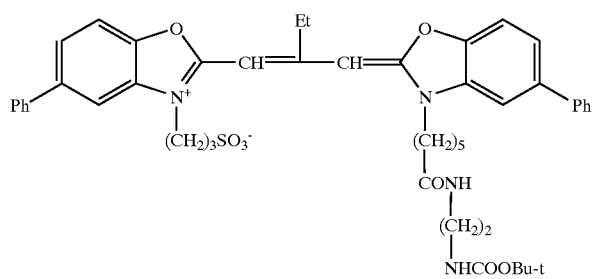
No. 82
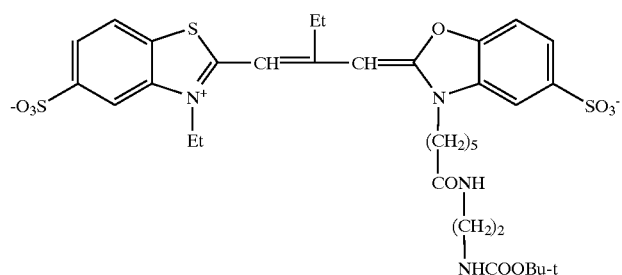
No. 83

No. 84
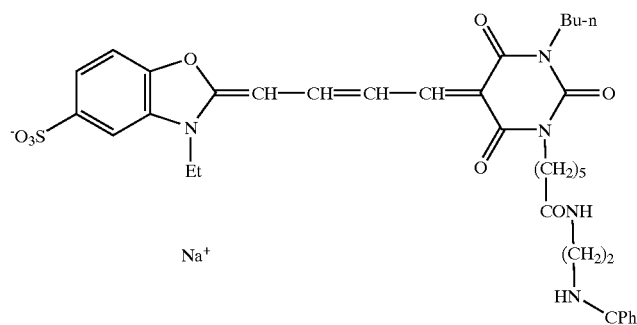
No. 85
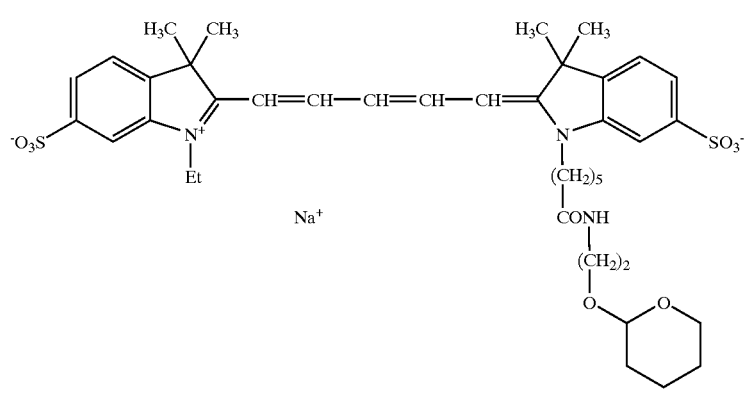
No. 86
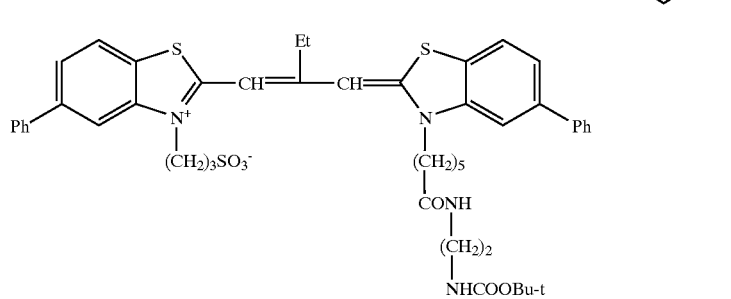
No. 87
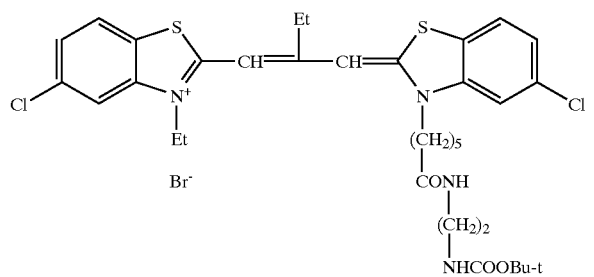
No. 88
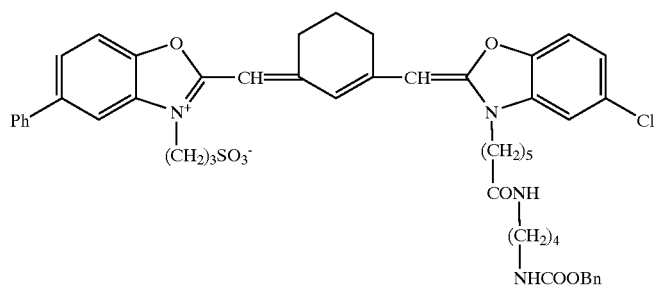

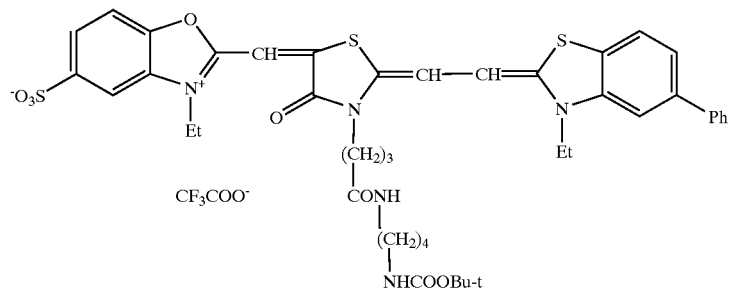

Suitable examples of present compounds represented by formula (4), those represented by formula (6) and those represented by formula (7) are shown below. However, these examples should not be construed as limiting the scope of the present invention. Additionally, the structural formulae of the present compounds as shown below are each no more than one extreme structure among many resonance structures each of the present compounds can take, and so each compound may take another resonance structure.

<Examples of a Compound Represented by Formula (4)>

<Examples of a Compound Represented by Formula (6)>

<Examples of a Compound Represented by Formula (7)>

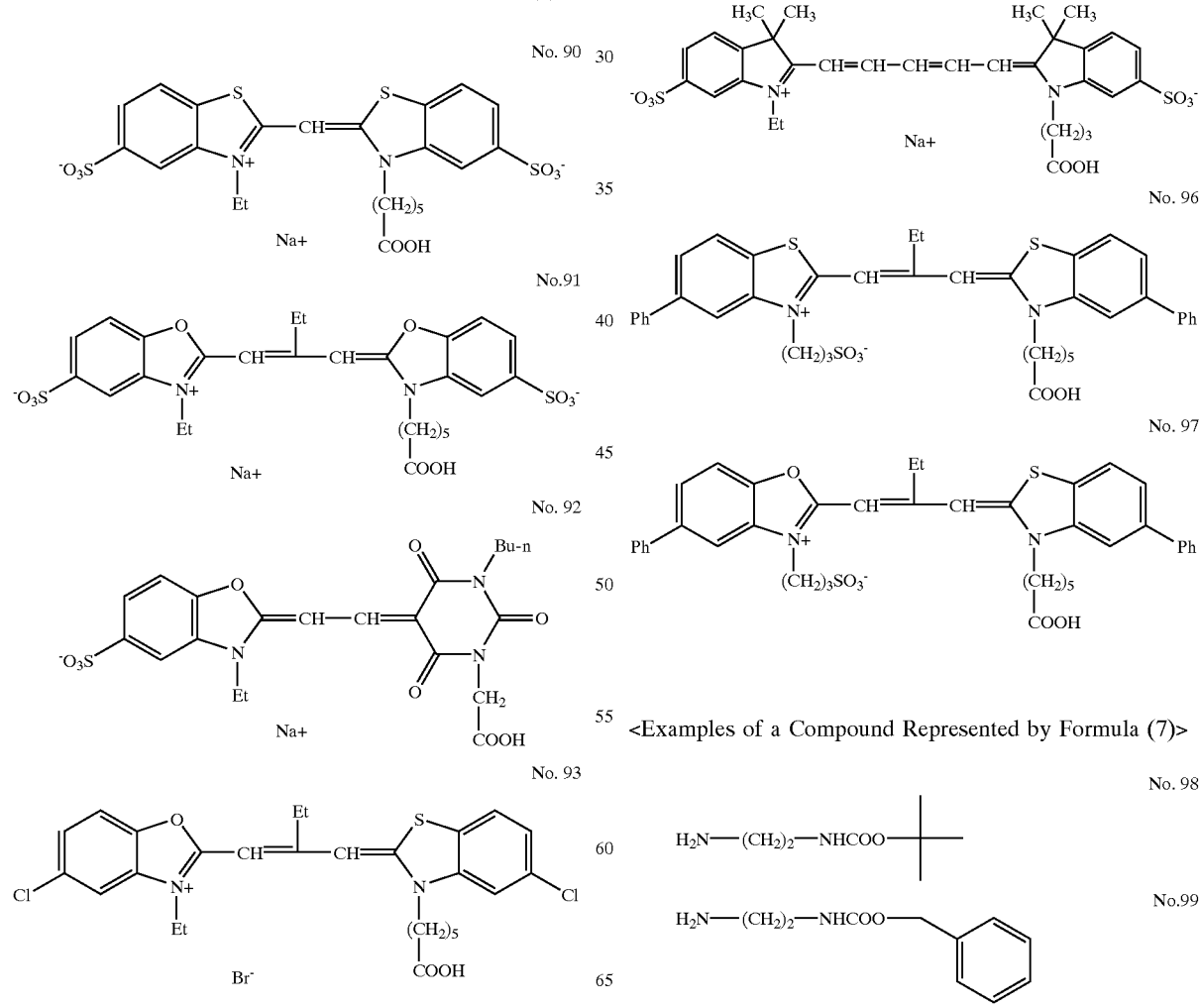

-continued

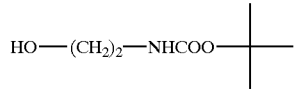
No.100

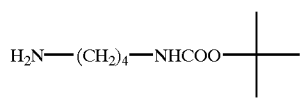
No. 101

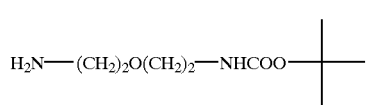
No. 102

Secondly, manufacturing methods of the present invention are explained.

The expression "manufacturing method" refers to a method including a step fitting into at least one among the broadly divided three methods as described below.

(1) A step of manufacturing a compound represented by formula (5) in accordance with the method described in claim 6.

(2) A step of manufacturing a compound represented by formula (3) in accordance with the method described in claim 5.

(3) A step of manufacturing a compound represented by formula (1) in accordance with the method described in claim 3.

Details of each method are described below in succession.

To begin with, the step (1) in which a compound represented by formula (5) is manufactured in accordance with the method specified in claim 6 is explained. This step consists in introducing a protected amino group from a dye carboxylic acid derivative. As far as the compound represented by formula (5) is produced after reaction between a compound represented by formula (6) and a compound represented by formula (7), the reaction may be performed under any conditions.

Any of methods known as amidation and esterification can be applied to the step (1). Examples of applicable methods include condensation with an acyl halide, mixed acid anhydride methods and methods of using various condensing agents. It is advantageous to use a condensing agent. Suitable examples of such a condensing agent include carbodiimides, 2-halopyridiniums, carbonates, uronium salts (e.g., O-(benzotriazole-1-yl)-N,N,N',N'-tetramethyluronium tetrafluoroborate), and phosphonium salts (e.g., BOP (benzotrizzole-1-yloxytris(dimethylamino) phosphonium hexa-fluorophosphate)).

This step is preferably carried out in a solvent. Any solvent may be used therein, but it is preferable to use THF, dichloromethane, acetonitrile, DMF, NMP or DMSO as the solvent.

And any temperature maybe chosen as a reaction temperature. Preferably, the reaction temperature is chosen from the range of from 0 to 150° C. Under the reaction temperature ranging from 0° C. to 150° C., the reaction time is preferably from 20 minutes to 10 hours, particularly preferably from 1 to 6 hours.

Then the step (2) in which a compound represented by formula (3) is manufactured in accordance with the method specified in claim 5 is explained.

All conditions including acidic, basic and other conditions are basically applicable to the step (2). However, the conditions suitable for this step depend on what kind of group is used as a protective group represented by P in formula (5).

It is therefore appropriate that methods suitable for the protective group used be selected from the book entitled "Protective Groups in Organic Synthesis", written by Theodora W. Greene and Peter G. M. Wuts, published by John Wiley & Sons Co. in New York and London.

In addition to the protective group limitation, it is preferable to select conditions with consideration given to the stability of dye chromophores. Providing a conscious description of conditions especially preferred in such a respect, anhydrous acidic conditions fit into them. In many of the particular cases where the protective groups lose their protecting functions by reaction with trifluoroacetic acid, it is appropriate to use trifluoroacetic acid at temperatures of from −20° C. to around room temperature (wherein the suitable reaction time is from 3 minutes to 3 hours, preferably from 5 minutes to 1 hour). However, the applicable conditions should not be construed as being limited to the aforedescribed ones.

Lastly, the step (3) in which a compound represented by formula (1) is manufactured in accordance with the method specified in Embodiment (3) is explained.

To this step also, any of methods known as the so-called amidation and esterification can be applied. Examples of such methods include condensation with acyl halides, mixed acid anhydride methods and methods of using various condensing agents. The use of condensing agents is preferred. Suitable examples of condensing agents include carbodiimides, 2-halopyridiniums, carbonates, uronium salts (e.g., O-(benzotriazole-1-yl)-N,N,N',N'-tetramethyluronium tetra-fluoroborate), and phosphonium salts (e.g., BOP (benzotrizzole-1-yloxytris(dimethylamino) phosphonium hexa-fluorophosphate)).

This step is preferably carried out in a solvent. Any solvent may be used therein, but it is preferable to use THF, dichloromethane, acetonitrile, DMF, NMP or DMSO as the solvent.

And any temperature maybe chosen as a reaction temperature. Preferably, the reaction temperature is chosen from the range of from 0 to 150° C. Under the reaction temperature ranging from 0° C. to 150° C., the reaction time is preferably from 20 minutes to 10 hours, particularly preferably from 1 to 6 hours.

The present compounds can be synthesized according to the methods described in the literature, such as F. M. Harmer, *Heterocyclic Compounds—Cyanine Dyes and Related Compounds*, John & Wiley & Sons, New York, London (1964), D. M. sturmer, *Heterocyclic Compounds—Special Topics in Heterocyclic Chemistry*, chapter 18, paragraph 14, pages 482–515, John & Wiley & Sons, New York, London (1977), and EP-A1-887700.

In the compounds represented by formula (1), it is preferable that Dye1 be greater than Dye2 in adsorptive strength to silver halide grains. In this respect, it is advantageous that Dye2 contains at least one —$SO_3M$, —$OSO_3M$. —$OPO_3M_2$ or —COOM, preferably at least one —$SO_3M$. Herein, M represents a proton or a cation.

Additionally, the adsorption strength of each dye moiety to silver halide grains can be estimated by the use of an individual model compound.

Further, it is preferable that optical excitation of Dye2 in a compound represented by formula (1) can cause electron or energy transfer to Dye1.

In silver halide photographic emulsions and silver halide photosensitive materials, it is advantageous that the compounds represented by formula (1) are adsorbed to silver halide grains via their respective Dye1 moieties, and besides, electron transfer or energy transfer to Dye1 is caused by optical excitation of Dye2 which is not adsorbed to silver halide grains.

Further, it is highly advantageous that the compounds represented by formula (1) are adsorbed to silver halide grains via their respective Dye1 moieties and form J-aggregates in silver halide photographic emulsions or silver halide photosensitive materials.

Next the present silver halide photographic materials are described below in detail.

The present compounds (i.e., the compounds of the present invention) are mainly used as sensitizing dyes in silver halide photographic emulsions and silver halide photographic materials.

In the silver halide photographic emulsions and the silver halide photographic materials, the present compounds can be used independently, in combination of two or more thereof, or in combination with other sensitizing dyes. Suitable examples of dyes usable therein include cyanine dyes, merocyanine dyes, rhodacyanine dyes, trinuclear merocyanine dyes, tetranuclear merocyanine dyes, allopolar dyes, hemicyanine dyes and styryl dyes. Of these dyes, cyanine dyes, merocyanine dyes and rhodacyanine dyes, especially cyanine dyes, are preferred over the others. Details of these dyes are described in F. M. Harmer, *Heterocyclic Compounds—Cyanine Dyes and Relalted Compounds*, John & Wiley & Sons, New York, London (1964), and D. M. sturmer, *Heterocyclic Compounds—Special Topics in Heterocyclic Chemistry*, chapter 18, paragraph 14, pages 482–515.

Suitable examples of dyes include the sensitizing dyes shown as general formulae and examples in U.S. Pat. No. 5,994,051, pages 32–44, and U.S. Pat. No. 5,747,236, pages 30–39.

The general formulae of cyanine dyes, merocyanine dyes and rhodacyanine dyes which are preferred in the present invention include the formulae (XI), (XII) and (XIII) illustrated in U.S. Pat. No. 5,340,694, columns 21 and 22 (provided that the numbers represented by n12, n15, n17 and n18 respectively are each an integer of 0 or above and have no limitations (but preferably 4 or below)).

These sensitizing dyes may be used alone, or as combinations of two or more thereof. Combinations of sensitizing dyes are often used for the purpose of supersensitization. The typical examples thereof are disclosed, e.g., in U.S. Pat. Nos. 2,688,545, 2,977,229, 3,397,060, 3,522,052, 3,527,641, 3,617,293, 3,628,964, 3,666,480, 3,672,898, 3,679,428, 3,303,377, 3,769,301, 3,814,609, 3,837,862 and 4,026,707, British Patent Nos. 1,344,281 and 1,507,803, Japanese Patent Publication No. 49336/1968, Japanese Patent Publication No. 12375/1978, and Japanese Patent Application (Laid-Open) Nos. 110618/1977 and 109925/1977.

In combination with sensitizing dyes, dyes having no spectrally sensitizing action by themselves or substances having substantially no absorption in the visible region but showing supersensitization may be incorporated in emulsions.

Supersensitizers useful in spectral sensitization relating to the present invention (e.g., pyrimidylamino compounds, triazinylamino compounds, azolium compounds, aminostyryl compounds, aromatic organic acid-formaldehyde condensates, azaindene compounds, cadmium salts), and combinations of supersensitizers and sensitizing dyes include those disclosed, e.g., in U.S. Pat. Nos. 3,511,664, 3,615,613, 3,615,632, 3,615,641, 4,596,767, 4,945,038, 4,965,182, 4,965,182, 2,933,390, 3,635,721, 3,743,510, 3,617,295 and 3,635,721. And the directions suitable for using them are those described in the patents described above.

The addition timing of the present sensitizing dyes (and those of other sensitizing dyes and supersensitizers also) may be at any of steps for emulsion-making as far as the steps are recognized as being useful. Specifically, as described in U. S. Pat. Nos. 2,735,766, 3,628,960, 4,183,756 and 4,225,666, and Japanese Patent Application (Laid-Open) Nos. 184142/1983 and 196749/1985, the sensitizing dyes and the supersensitizers may be added at the step of forming silver halide grains or/and during a period before desalting, or at the desalting step and/or during a period from the end of desalting to the start of chemical ripening. Also, as described in Japanese Patent Application (Laid-Open) No. 113920/1983, they may be added during a period just before chemical ripening or at the chemical ripening step, or during any period or step before coating of chemically ripened emulsions. In addition, as disclosed in U.S. Pat. No. 4,225,666 and Japanese Patent Application (Laid-Open) No. 7629/1983, it is permitted to divide the addition amount of one compound alone or a combination of compounds having different structures into several portions, and add these portions at the grain formation step and the chemical ripening step or the conclusion of chemical ripening, respectively, or before, during and after the chemical ripening, respectively. In divided addition, compounds or combinations of compounds added may also vary in kind from step to step, or from period to period.

The addition amount of the sensitizing dyes of the present invention (and those of other sensitizing dyes and supersensitizers as well) depends on the shape and size of silver halide grains, and can stand at any value. However, it is appropriate that they be added in an amount of $1 \times 10^{-8}$ to $8 \times 10^{-1}$ mole per mole of silver halide. More specifically, when the size of silver halide grains is from 0.2 to 1.3 $\mu$m, the suitable addition amount is from $2 \times 10^{-6}$ to $3.5 \times 10^{-3}$ mole, preferably from $7.5 \times 10^{-6}$ to $1.5 \times 10^{-3}$ mole, per mole silver halide.

The sensitizing dyes of the present invention (and other sensitizing dyes and supersensitizers as well) can be dispersed directly into emulsions. On the other hand, they may be dissolved first in an appropriate solvent, such as methyl alcohol, ethyl alcohol, methyl cellosolve, acetone, water, pyridine or a mixture of two or more thereof, and then added to emulsions. These procedures may be carried out in the presence of additives, such as bases, acids or surfactants. In addition, ultrasonic waves can be used for the dissolution. In adding the compounds to emulsions, various methods can be adopted. Examples of such methods include the method as disclosed in U.S. Pat. No. 3,469,987, which includes steps of dissolving the compounds in a volatile organic solvent, dispersing the solution into a hydrophilic colloid and adding the dispersion to an emulsion; the method as disclosed in Japanese Patent Publication No. 24185/1971, which includes steps of dispersing the compounds into a water-soluble solvent and adding the dispersion into an emulsion; the method as disclosed in U.S. Pat. No. 3,822,135, which includes steps of dissolving the compounds in a surfactant and adding the solution to an emulsion; the method as disclosed in Japanese Patent Application (Laid-Open) No. 74624/1976, which includes steps of dissolving the compounds with the aid of a red-sift compound and adding the solution to an emulsion; and the method as disclosed in Japanese Patent Application (Laid-Open) No. 80826/1975, which includes steps of dissolving the compounds in a substantially water-free acid and adding the solution to an emulsion. In addition to these methods, the methods disclosed in U.S. Pat. Nos. 2,912,343, 3,342,605, 2,996,287 and 3,429,835 can also be employed in adding the compounds to emulsions.

In photographic emulsions responsible for photosensitive mechanism, any of silver bromide, silver iodobromide, silver chlorobromide, silver iodide, silver iodochloride, silver iodobromochloride and silver chloride may be used as silver halide. On the other hand, a firm multilayer adsorption structure can be formed when the iodide constitutes at least 0.1 mole %, preferably at least 1 mole %, particularly preferably at least 5 mole %, of the halide composition at the outermost surface of emulsion grains.

The size distribution of grains may be broad or narrow. However, a narrow size distribution is preferred in the present invention.

The silver halide grains of a photographic emulsion may have any of crystal shapes, including regular crystal shapes such as those of a cube, an octahedron, a tetradecahedron and an orthorhombic dodecahedron, irregular crystal shapes such as those of a sphere and a tablar, and crystal shapes having an (hkl) plane. In addition, a mixture of grains having those different crystal shapes may be present in a photographic emulsion. However, the use of tabular grains is preferred in the present invention. And details of tabular grains are described below. For the grains having high-index surfaces *Journal of Imaging Science*, vol. 30, pp. 247–254 (1986) can be referred to.

The silver halide grains described above may be present alone or as a mixture of two or more thereof in each of silver halide photographic emulsions used in the present invention. The silver halide grains used may be different in halide composition between the interior and the surface layer thereof, or they may have a multi-phase structure wherein junctions are present, or they may have localized phases at the grain surface, or they may be uniform throughout in halide composition. In addition, the grains different in the distribution of halide composition may be used as a mixture.

These various emulsions maybe emulsions of the kind which form latent images predominantly at the grain surfaces, or those of the kind which mainly form latent images inside the grains.

The suitable halide composition of tabular silver halide grains used in the present invention is chloride, bromide, chlorobromide, iodobromide, chloroiodobromide or chloroiodide. It is desirable for the tabular grains to have (100) or (111) surfaces as the main surfaces. The tabular grains having (111) main surfaces are referred to as (111) tabular grains hereinafter. The (111) tabular grains generally have triangular or hexagonal surfaces. In general, the proportion of grains having hexagonal surfaces becomes higher the more uniform the grains are in size distribution. The details of monodisperse hexagonal tabular grains are described in Japanese Patent Publication No. 61205/1993.

The tabular grains having (100) surfaces as the main surfaces, hereinafter referred to as (100) tabular grains, have rectangular or square surfaces. As to these emulsion grains, grains whose adjacent edges have a ratio less than 5:1 are referred to as tabular grains rather than acicular grains. When the halide composition of tabular grains is chloride or rich in chloride, the (100) tabular grains essentially have higher main surface stability than the (111) tabular grains. In the case of (111) tabular grains, it is required to stabilize the (111) main surfaces. The methods for stabilizing these surfaces are disclosed in Japanese Patent Application (Laid-Open) Nos. 80660/1997 and 80656/1997, and U.S. Pat. No. 5,298,388.

The (111) tabular silver chloride grains and the (111) tabular silver halide grains having high chloride contents, which are usable in the present invention, are disclosed, e.g., in U.S. Pat. Nos. 4,414,306, 4,400,463, 4,713,323, 4,783, 398, 4,962,491, 4,983,508, 4,804,621, 5,389,509, 5,217,858 and 5,460,934.

The (111) silver halide tabular grain shaving high bromide contents, which are usable in the present invention, are disclosed, e.g., in U.S. Pat. Nos. 4,425,425, 4,425,426, 4,434,226, 4,439,520, 4,414,310, 4,433,048, 4,647,528, 4,665,012, 4,672,027, 4,678,745, 4,684,607, 4,593,964, 4,722,886, 4,722,886, 4,755,617, 4,755,456, 4,806,461, 4,801,522, 4,835,322, 4,839,268, 4,914,014, 4,962,015, 4,977,074, 4,985,350, 5,061,609, 5,061,616, 5,068,173, 5,132,203, 5,272,048, 5,334,469, 5,334,495, 5,358,840 and 5,372,927.

The (100) tabular grains usable in the present invention are disclosed, e.g., in U.S. Pat. Nos. 4,386,156, 5,275,930, 5,292,632, 5,314,798, 5,320,938, 5,319,635 and 5,356,764, European Patent Nos. 569971 and 737887, and Japanese Patent Application (Laid-Open) Nos. 308648/1994 and 5911/1997.

The silver halide emulsion grains used in the present invention are preferably tabular silver halide grains having a higher surface area/volume ratio to which the sensitizing dyes disclosed in the present invention are adsorbed. The suitable aspect ratio of such tabular grains is at least 2, preferably at least 5, particularly preferably at least 8. And the tabular grains used in the present invention have no particular limitation as to the upper limit of the aspect ratio. However, it is appropriate that the aspect ratio be at most 1,000, preferably not higher than 500. The suitable thickness of the tabular grains is smaller than 0.2 $\mu$m, preferably smaller than 0.1 $\mu$m, particularly preferably smaller than 0.07 $\mu$m.

The expression "the aspect ratio is at least 2" as used herein means that silver halide grains having aspect ratios (ratios of equivalent circle diameter of grain/thickness of grain) of at least 2 are present in an emulsion in a proportion of at least 50%, on a projected area basis, to the total silver halide grains in the emulsion. In emulsions used in the present invention, it is advantageous that the proportion of silver halide grains having aspect ratio of at least 2 to the total silver halide grains is at least 70%, preferably at least 85%.

For preparing thin tabular grains having such high aspect ratios, the following arts are applicable.

It is appropriate that the tabular grains used in the present invention be uniform in distribution of dislocation lines amount among the grains. In the emulsions used in the present invention, it is advantageous that silver halide grains having at least 10 dislocation lines per grain constitute, on a number basis, 100 to 50%, preferably 100 to 70%, particularly preferably 100 to 90%, of the total grains. When the proportion of the grains having at least 10 dislocation lines per grain is lower than 50% in an emulsion, the emulsion is undesirable because the grains therein lack uniformity.

In determination of the proportion of grains containing dislocation lines and the number of dislocation lines, it is appropriate that dislocation lines formed in at least 100 grains each, preferably at least 200 grains each, particularly preferably at least 300 grains each, be observed.

As protective colloids used at the time of making the present emulsions and binders of other hydrophilic colloid layers, gelatin is used to advantage, but other hydrophilic colloids can be also be utilized.

Examples of hydrophilic colloids usable therein include proteins, such as gelatin derivatives, graft polymers prepared from gelatin and other macromolecules, albumin and casein; sugar derivatives, such as cellulose derivatives including hydroxyethyl cellulose, carboxymethyl cellulose and cellulose sulfates, sodium alginate and starch derivatives; and various kinds of synthetic hydrophilic homo- and copolymers, such as polyvinyl alcohol, partial acetals of polyvinyl alcohol, poly-N-vinylpyrrolidone, polyacrylic acid, polymethacrylic acid, polyacrylamide, polyvinyl imidazole, polyvinyl pyrazole.

As gelatins, not only lime-processed gelatin but also acid-processed gelatin and enzyme-processed gelatin as described in *Bull. Soc. Sci. Photo. Japan*, No. 16, p. 30 (1966) may be used. And hydrolysis products of gelatin and enzyme-decomposed products of gelatin can also be used.

The present emulsions are preferably subjected to washing for removal of salts, and then dispersed into newly prepared protective colloids. The washing temperature can be chosen depending on the intended use of the emulsions to be washed. Preferably, the washing is carried out at a temperature ranging from 5° C. to 50° C. The pH at the time of washing can also be chosen depending on the intended use of the emulsions to be washed. It is appropriate to choose the pH from the range of 2 to 10, preferably the range of 3 to 8. Further, the pAg at the time of washing can also be chosen depending on the intended use of the emulsions to be washed. Preferably, the pAg is chosen from the range of 5 to 10. The method of washing can be chosen from among known methods including the noodle washing method, the dialysis using a semi-permeable membrane, the centrifugal separation method, the flocculation sedimentation method and the ion exchange method. When the flocculation sedimentation method is adopted, the sedimentation agent used therein can be selected from sulfates, organic solvents, water-soluble polymers or gelatin derivatives.

At the time of preparing the present emulsions, e.g., at the time of forming silver halide grains, at the desalting step, at the chemical sensitization step or before the emulsions are coated, the presence of salts of metal ions is preferable, depending on the desired purposes. It is appropriate that the salts be added at the time of grain formation in the case of doping the grains with them, while they be added during the period from after the grain formation to before the conclusion of chemical sensitization in the case of using them for modification of the grain surface or as chemical sensitizers. In the case of doping, it is allowable to select one from among three methods, namely the method of doping throughout the grains, the method of doping only the core part of the grains and the method of doping only the shell part of the grains. Examples of a metal ion usable for doping include ions of Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb and Bi. These metals can be added as far as they assume the forms of salts capable of dissolving at the time of grain formation, such as ammonium salts, acetates, nitrates, sulfates, phosphates, hydroxides, six-coordinated complex salts and four-coordinated complex salts. Examples of such salts include $CdBr_2$, $CdCl_2$, $Cd(NO_3)_2$, $Pb(NO_3)_2$, $Pb(CH3COO)_2$, $K_2[Fe(CN)_6]$, $(NH_4)_4[Fe(CN)_6]$, $K_3IrCl_6$, $(NH_4)_3RhCl_6$ and $K_4Ru(CN)_6$. The ligands of coordination compounds can be selected from among halo, aquo, cyano, cyanato, thiocyanato, nitrosyl, thionitrosyl, oxo and carbonyl. These metal compounds may be used alone or as combinations of two or more thereof.

Those metal compounds are dissolved in water or an appropriate organic solvent, such as methanol or acetone, and then added to emulsions. For stabilizing the solution, it is possible to use the method of adding an aqueous solution of hydrogen halide (e.g., HCl, HBr) or alkali halide (e.g., KCl, NaCl, KBr, NaBr). Further, acids or alkalis may be added, if needed. The metal compounds may be added to a reaction vessel before the grain formation or in the course of grain formation. In another way, the metal compounds are added to an aqueous solution of water-soluble silver salt (e.g., $AgNO_3$) or alkali halide (e.g., NaCl, KBr, KI), and thereby continuous addition thereof can be carried out over a period of grain formation. In still another way, a solution of metal compound is prepared independently of the solutions of water-soluble silver salt and alkali halide, and may be added continuously during an appropriate period. In addition, the combined use of various ways to add metal compounds is also favorable.

As disclosed in U.S. Pat. No. 3,772,031, the method of adding chalcogen compounds during the emulsion-making is useful in some cases. In addition to S, Se and Te, cyan salts, thiocyan salts, selenocyan salts, carbonates, phosphates and acetates may be present at the time of emulsion-making.

At any step of the process for preparing silver halide emulsions, the present silver halide grains can be subjected to at least one kind of sensitization selected from among sulfur sensitization, selenium sensitization, gold sensitization, palladium sensitization, sensitization with other noble metals, and reduction sensitization. It is advantageous to combine two or more of sensitization methods. Various types of emulsions can be prepared depending on what step the chemical sensitization is performed. For instance, there are three types of emulsions, namely an emulsion whose chemical sensitization specks are embedded in the interior of the grains, an emulsion whose chemical sensitization specks are embedded in a zone close to the grain surface, and an emulsion whose chemical sensitization specks are present at the grain surface. The present emulsions can choose the location for chemical sensitization specks depending on the desired purposes. However, it is generally preferable to form at least one kind of chemical sensitization specks in the vicinity of the grain surface.

The chemical sensitization advantageously carried out in the present invention is chalcogen sensitization, noble metal sensitization, or a combination of these sensitization methods. Specifically, such sensitization can be effected by the use of activated gelatin as described in T. H. James, *The Theory of the Photographic Process*, 4th ed., pp. 67–76, Macmillan (1977), or by using a sulfur sensitizer, a selenium sensitizer, a tellurium sensitizer, a gold sensitizer, a platinum sensitizer, a palladium sensitizer, an iridium sensitizer or a combination of two or more of these sensitizers under the pAg of 5–10, the pH of 5–8 and the temperature of 30 to 80° C. as disclosed in *Research Disclosure*, vol. 120, item 12008 (April 1974), *Research Disclosure*, vol. 34, item 13452 (June 1975), U.S. Pat. Nos. 2,642,361, 3,297,446, 3,772,031, 3,857,711, 3,901,714, 4,266,018 and 3,904,415, and British Patent No. 1,315,755. In the noble metal sensitization, salts of noble metals, such as gold, platinum, palladium and iridium, can be used. Of these sensitization methods, gold sensitization, palladium sensitization and the combination thereof are preferred over the others. In the case of gold sensitization, well-known compounds including chloroauric acid, potassium chloroaurate, potassium aurithiocyanate, gold sulfide and gold selenide can be used. The palladium compounds are intended to include salts of divalent palladium and salts of tetravalent palladium. The palladium compounds preferred herein are represented by $R_2PdX_6$ or $R_2PdX_4$. Herein, R represents a hydrogen atom, an alkali metal atom or an ammonium group, and X represents a halogen atom such as chlorine atom, bromine atom or iodine atom.

Suitable examples of such a palladium compound include $K_2PdCl_4$, $(NH_4)_2PdCl_6$, $Na_2PdCl_4$, $(NH_4)_2PdCl_4$, $Li_2PdCl_4$, $Na_2PdCl_6$ and $K_2PdBr_4$. The gold compounds and the palladium compounds are preferably used in combination with thiocyanates or selenocyanates.

Examples of a sulfur sensitizer usable in the present invention include hypo, thiourea compounds, rhodanine compounds and the sulfur-containing compounds disclosed in U.S. Pat. Nos. 3,857,711, 4,266,018 and 4,054,457. The chemical sensitization can also be effected in the presence of the so-called chemical sensitization assistants. The compounds useful as these assistants include compounds known to prevent fogging and increase sensitivity in the process of chemical sensitization, such as azaindene, azapyridazine and azapyrimidine. Examples of a chemical sensitization assistant modifier are described in U.S. Pat. Nos. 2,131,038, 3,411,914 and 3,554,754, Japanese Patent Application (Laid-Open) No. 126526/1983, and G. F. Duffin, Photographic Emulsion Chemistry, pp. 138–143, The Focal Press, London (1966).

It is preferable for the present emulsions to undergo gold sensitization also. The suitable amount of a gold sensitizer used is from $1 \times 10^{-4}$ to $1 \times 10^{-7}$ mole, preferably from $1 \times 10^{-5}$ to $1 \times 10^{-7}$ mole, per mole of silver halide. The suitable amount of a palladium compound used is from $1 \times 10^{-3}$ to $5 \times 10^{-7}$ mole, and that of a thiocyan or selenocyan compound used is from $5 \times 10^{-3}$ to $1 \times 10^{-6}$ mole.

The suitable amount of a sulfur sensitizer used for the present silver halide grains is from $1 \times 10^{-4}$ to $1 \times 10^{-7}$ mole, preferably from $1 \times 10^{-5}$ to $5 \times 10^{-7}$ mole, per mole of silver halide.

Selenium sensitization is included in the sensitization methods suitable for the emulsions of the present invention. In the selenium sensitization, well-known labile selenium compounds are used. Specifically, selenium compounds, such as colloidal metallic selenium, selenoureas (e.g., N,N-dimethylselenourea, N,N-diethylselenourea), selenoketones and selenoamides, can be used as seleninum sensitizers. In some cases, it is advantageous that the selenium sensitization is carried out in combination with sulfur sensitization, noble metal sensitization or both of them.

It is preferable for the present silver halide emulsions to undergo reduction sensitization during the grain formation, or during a period from the end of grain formation to the start of chemical sensitization, or during the chemical sensitization, or after the chemical sensitization.

For effecting the reduction sensitization during those periods, any of the method of adding a reduction sensitizer to a silver halide emulsion, the method of performing growth or ripening of grains in the low pAg atmosphere of pAg 1–7, referred to as "silver ripening", and the method of performing growth or ripening of grains in the high pH atmosphere of pH 8–11, referred to as "high pH ripening", may be chosen. In addition, two or more of those methods may be used in combination.

The method of adding a reduction sensitizer has an advantage in enabling a delicate adjustment of reduction sensitization level.

Examples of known reduction sensitizers include stannous salts, ascorbic acid and derivatives thereof, amines and polyamines, hydrazine derivatives, formamidinesulfinic acid, silane compounds and borane compounds. The compounds used for the reduction sensitization of the present invention can be selected from those known compounds, and two or more of the compounds may be used in combination. The compounds preferred as reduction sensitizers are stannous chloride, thiourea dioxide, dimethylamineborane, and ascorbic acid and its derivatives. It is required to properly choose the amount of a reduction sensitizer added, because the amount to be added depends on the emulsion-making conditions. The suitable addition amount is generally in the range of $10^{-7}$ to $10^{-3}$ mole per mole of silver halide.

The reduction sensitizer or sensitizers are dissolved in water or an organic solvent, such as an alcohol compound, glycols, ketones, esters or amides, and added during the grain growth. Such a solution may be added in advance to a reaction vessel, but it is preferably added in an appropriate stage of the grain growth. In one preferred way, silver halide grains may be precipitated by the use of reduction sensitizer (s) previously added to an aqueous solution of water-soluble silver salt or water-soluble alkali halide. In another preferred way, a solution of reduction sensitizer(s) is added in several portions while the grain growth is in progress, or it is added continuously over a long period.

Further, it is preferable to use an oxidizing agent for silver in the process of preparing the emulsions of the present invention. The term "an oxidizing agent for silver" as used herein refers to a compound capable of acting on metallic silver to convert it into silver ion. The compounds especially useful as the oxidizing agent are those capable of converting extremely fine silver grains, which are formed as a by-product at the step of grain formation and chemical sensitization of silver halide, into silver ions. The silver ions produced herein may form slightly soluble salts, such as silver halides, silver sulfide and silver selenide, or they may form water-soluble salts, such as silver nitrate. The oxidizing agents for silver may be either inorganic substances or organic substances. Examples of an inorganic oxidizing agent for silver include ozone; hydrogen peroxide and adducts thereof (e.g., $NaBO_2.H_2O_2.3H_2O$, $2NaCO_3.3H_2O_2$, $Na_4P_2O_7.2H_2O_2$ and $2Na_2SO_4.H_2O_2.2H_2O$); oxoacid salts, such as peroxoacid salts (e.g., $K_2S_2O_8$, $K_2C_2O_6$ and $K_2P_2O_8$), peroxo complex compounds (e.g., $K_2[Ti(O_2) C_2O_4].3H_2O$, $4K_2SO_4.Ti(O_2)OH.SO_4.2H_2O$ and $Na_3[VO (O_2)(C_2H_4)_2].6H_2O$), permanganates (e.g., $KMnO_4$) and chromates (e.g., $K_2Cr_2O_7$); halogen elements, such as iodine and bromine; perhalogenates (e.g., potassium periodate); salts of high-valent metals (e.g., potassium hexacyanoferrate (III)); and thiosulfonates.

Examples of an organic oxidizing agent for silver include quinones (e.g., p-quinone), organic peroxides (e.g., peracetic acid, perbenzoic acid), and active halogen-releasing compounds (e.g., N-bromosuccinimide, Chloramine T, Chloramine B).

The oxidizing agents preferably used in the present invention are inorganic oxidizing agents including ozone, hydrogen peroxide and adducts thereof, halogen elements and thiosulfonates, and organic oxidizing agents including quinones. The combined use of the reduction sensitization as described above and the oxidizing agent for silver as described above is a preferred embodiment of the present invention. Therein, it is allowable to adopt any of the method in which the reduction sensitization is carried out after the oxidizing agent is used, the method in which these procedures are performed in inverse order, and the method in which both procedures are carried out at the same time. These methods can be applied at the step of either grain formation or chemical sensitization.

The photographic emulsions used in the present invention can contain a wide variety of compounds for purposes of preventing fogging or stabilizing photographic properties during production, storage or photographic processing of the photosensitive material of the present invention. Specifically, many compounds known as antifoggants and stabilizers, such as thiazoles (e.g., benzothiazolium salts), nitroindazoles, nitrobenzimidazoles, chlorobenzimidazoles, bromobenzimida-zoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), mercapto-pyrimidines, mercaptotriazines, thioketo compounds (e.g., oxazolinethione) and azaindenes (e.g., triazaindenes, tetraazaindenes (especially 1,3,3a,7-tetraazaindenes substituted with a hydroxyl group at the 4-position) and pentaazaindenes), can be added. More specifically, the compounds as disclosed in U.S. Pat. Nos. 3,954,474 and 3,982,947, and Japanese Patent Publication No. 28660/1977 can be used. The compound disclosed in Japanese Patent Application (Laid-Open) No. 212932/1988 is also one of compounds suitable for the foregoing purposes. The antifoggants and the stabilizers can be added at various periods depending on the intended purposes. For instance, they can be added before the grain formation, during the grain formation, after the grain formation, at the washing step, at the time of dispersion after washing, before the chemical sensitization, during the chemical sensitization, or before the coating. Besides producing intrinsic antifogging and stabilizing effects, the antifoggants and the stabilizers added during the emulsion-making can be utilized for many purposes including crystal habit control of grains, reduction of grain size, decrease in solubility of grains, control of chemical sensitization and control of dye alignment.

The silver halide emulsions prepared according to the present invention can be applied to any of color photographic materials and black-and-white photographic materials. In particular, color photographic paper, color films for picture taking, color reversal films and color diffusion transfer films are suitable as the color photographic materials to which the present emulsions are applied. As examples of the black-and-white photographic materials, mention may be made of picture-taking films for amateur use, X-ray films, films for medical diagnosis, photosensitive films for graphic arts, and diffusion transfer films.

In the fields of films for medical diagnosis and photosensitive films for graphic arts, the use of a laser image setter or a laser imager enables effective exposure.

The techniques applicable in those fields are disclosed, e.g., in Japanese Patent Application (Laid-Open) Nos. 287337/1995, 335342/1992, 313289/1993, 122945/1996 and 292512/1996.

Further, the present silver halide emulsions can be applied to heat-developable photosensitive materials. The materials known as heat-developable photosensitive materials have photosensitive layers which each contain a catalytically active amount of photo-catalyst (e.g., silver halide), a reducing agent and a reducible silver salt (e.g., an organic silver salt), and further a color toning agent for controlling the silver tone, if needed, in a condition that they are dispersed in a binder matrix. Descriptions of those materials can be found, e.g., in U.S. Pat. Nos. 3,152,904, 3,457,075, 2,910,377 and 4,500,626, Japanese Patent Application (Laid-Open) Nos. 4924/1968, 24200/1999, 24201/1999, 30832/1999, 84574/1999, 65021/1999, 109547/1999, 125880/1999, 129629/1999, 133536/1999, 133537/1999, 133538/1999, 133539/1999, 133542/1999, 133543/1999, 223898/1999, 352627/1999, 130607/1994, 332134/1994, 332136/1994, 347970/1994, 261354/1995 and 281785/2001.

The present compounds can be suitably used in diffusion transfer photosensitive materials. For details of materials according to a heat-developable diffusion transfer process, Japanese Patent application (Laid-Open) Nos. 98562/2000 (using preformed dyes) and 281785/2001 (using coupling formation dyes) can be referred to. And for materials according to an instant photographic process the method described in Japanese Patent Application (Laid-Open) No. 284442/2000 can be referred to.

To preparation methods for photographic emulsions used in the present invention, the descriptions in Japanese Patent Application (Laid-Open) No. 239789/1998, column 63, 36th line, to column 65, 2nd line, can be applied.

To additives like color couplers, additives for photographic materials, types of photosensitive materials to which the present invention is applicable, and photographic processing of photosensitive materials, the descriptions in Japanese Patent Application (Laid-Open) No. 239789/1998, column 65, 3rd line, to column 73, 13th line, can be applied.

In addition to the various additives as described above, a wide variety of other additives can be used in the present silver halide photographic materials, depending on the desired purposes.

Details of these additives are described in *Research Disclosure*, Item 17643 (December 1978), ibid. Item 18716 (November 1979), and ibid. Item 308119 (December 1989). And the locations where the additives are described in each of those references are listed below.

| Kinds of Additives | RD-17643 | RD-18716 | RD-308119 |
|---|---|---|---|
| 1. Chemical sensitizer | p. 23 | p. 648, right column | p. 996 |
| 2. Sensitivity increasing agent | | p. 648, right column | |
| 3. Spectral sensitizer and Super-sensitizer | pp. 23–24 | p. 648, right column, to p. 649, right column | p. 996, right column, to p. 998, right column |
| 4. Brightening agent | p. 24 | | p. 998, right column |
| 5. Antifoggant and Stabilizer | pp. 24–25 | p. 649, right column | p. 998, right column, to p. 1000, right column |
| 6. Light absorbent, Filter dye, UV absorbent | pp. 25–26 | p. 649, right column, to p. 650, left column | p. 1003, left column to right column |
| 7. Stain inhibitor | p. 25, right column | p. 650, left column to | p. 1002, right column right column |
| 8. Dye image stabilizer | p. 25 | | p. 1002, right column |
| 9. Hardener | p. 26 | p. 651, left column | p. 1004, right column, to p. 1005, left column |
| 10. Binder | p. 26 | p. 651, left column | p. 1003, right column, to p. 1004, right column |
| 11. Plasticizer, Lubricant | p. 27 | p. 650, right column | p. 1006, left column to right column |
| 12. Coating aid, Surfactant | pp. 26–27 | p. 650, right column | p. 1005, left column, to p. 1006, left column |
| 13. Antistatic agent | p. 27 | p. 650, right column | p. 1006, right column, to p. 1007, left column |
| 14. Matting agent | | | p. 1008, left column, to p. 1009, left column |

The arts of arranging layers, silver halide emulsions, dye-forming couplers, functional couplers including DIR couplers, various kinds of additives and photographic processing which can be applied to the present emulsions and photographic materials using the present emulsions are described in EP-A1-0565096 (laid open in Oct. 13, 1993) and the patents cited therein. The locations where those items are described in the document are listed below.

1. Layer structure: p. 61, lines 23–35, and p. 61, line 41, to p. 62, line 14
2. Interlayer: p. 61, lines 36–40
3. Interlayer effect-providing layer: p. 62, lines 15–18
4. Halide composition of silver halide: p. 62, lines 21–25
5. Crystal habit of silver halide grains: p. 62, lines 26–30
6. Grain size of silver halide: p. 62, lines 31–34
7. Emulsion-making methods: p. 62, lines 35–40
8. Size distribution of silver halide grains: p. 62, lines 41–42
9. Tabular grains: p. 62, lines 43–46
10. Internal structure of grains: p. 62, lines 47–53
11. Types of latent image formation in emulsion: p. 62, line 54, to p. 63, line 5
12. Physical ripening and chemical sensitization of emulsions: p. 63, lines 6–9
13. Mixed use of emulsions: p. 63, lines 10–13
14. Fogged emulsions: p. 63, lines 14–31
15. Light-insensitive emulsions: p. 63, lines 32–43
16. Silver coverage: p. 63, lines 49–50
17. Formaldehyde scavengers: p. 64, lines 54–57
18. Mercapto-type antifoggants: p. 65, lines 1–2
19. Fogging agent releasers: p. 65, lines 3–7
20. dyes: p. 65, lines 7–10
21. Color couplers in general: p. 65, lines 11–13
22. Yellow, magenta and cyan couplers: p. 65, lines 14–25
23. Polymeric couplers: p. 65, lines 26–28
24. Diffusible dye forming couplers: p. 65, lines 29–31
25. Colored couplers: p. 65, lines 32–38
26. Functional couplers in general: p. 65, lines 39–44
27. Bleach accelerator releasing couplers: p. 65, lines 45–48
28. Development accelerator releasing couplers: p. 65, lines 49–53
29. Other DIR couplers: p. 65, line 54, to p. 66, line 4
30. Coupler dispersion methods: p. 66, lines 5–28
31. Antiseptic and fungicide: p. 66, lines 29–33
32. Kinds of photosensitive materials: p. 66, lines 34–36
33. Photosensitive layer thickness and swelling speed: p. 66, line 40, to p. 67, line 1
34. Backing layer: p. 67, lines 3–8
35. Development-processing in general: p. 67, lines 9–11
36. Developing solution and developing agent: p. 67, lines 12–30
37. Additives to developing solution: p. 67, lines 31–44
38. Reversal processing: p. 67, lines 45–56
39. Opening rates of processing solutions: p. 67, line 57, to p. 68, line 12
40. Development time: p. 68, lines 13–15
41. Blix-Bleach-Fixation: p. 68, line 16, to p. 69, line 31
42. Automatic developing machines: p. 69, lines 32–40
43. Washing-Rinsing-Stabilization: p. 69, line 41, to p. 70, line 18,
44. Replenishment-Reuse of processing solutions: p. 70, lines 19–23
45. Incorporation of developing agent in photosensitive material: p. 70, lines 24–33
46. Development-processing temperatures: p. 70, lines 34–38
47. Application to lens-equipped films: p. 70, lines 39–41

Exposure methods for the present silver halide photographic materials are explained below.

Exposure for obtaining photographic images may be performed in a usual manner. Specifically, various kinds of known light sources, such as natural light (sunlight), a tungsten lamp, a fluorescent lamp, a mercury lamp, a xenon arc lamp, a carbon arc lamp, a xenon flash lamp, laser, LED and CRT, can be employed. Further, the present photographic materials may be exposed to light emitted from a phosphor excited by electron beams, X-rays, γ-rays or α-rays.

Laser light sources are preferred in some embodiments of the present invention. Examples of a laser light source usable in the present invention include laser devices wherein helium-neon gas, argon gas, krypton gas and carbon dioxide gas are utilized respectively as laser oscillation media, laser devices using solid-state oscillation media, such as ruby and cadmium, liquid laser devices and semiconductor laser devices. Contrasted with light for usual illumination use, such laser light is coherent light having a single wavelength, an identical phase and a sharp directional property. Therefore, the silver halide photographic materials to undergo exposure to such laser light are required to have spectral characteristics corresponding to light-emission wavelengths of the laser devices used.

Of the laser devices described above, semiconductor laser devices are preferred over the other devices.

Besides being used as sensitizing dyes, the present compounds can be used as filter dyes for improving sharpness and color resolution, irradiation neutralizing dyes or antihalation dyes.

Into coating solutions for constituent layers of silver halide photographic materials, filter layers and/or antihalation layers, these compounds can be incorporated in usual manners. When the compounds are used as dyes, they are used in an amount large enough to color the photographic layers, and persons skilled in the art can easily determine the amount as appropriate according to the purpose of their use. In general, it is appropriate that the dyes be used in such an amount as to provide the optical density of 0.05 to 3.0. The addition time may be any of steps prior to coating.

Polymers having charges opposite in polarity to ions of the dyes may be added as a mordant to the layer in which the dyes are incorporated, and enable localization of the dyes to the specified layer through interaction with the dye molecules.

Examples of a polymer mordant usable for such a purpose include the polymers disclosed in U.S. Pat. Nos. 2,548,564, 4,124,386, 3,625,694, 3,958,995, 4,168,976 and 3,445,231.

Besides being incorporated in photosensitive emulsion layers, the present compounds can be added to other layers, such as an interlayer, a protective layer and a backing layer, if desired.

Further, the present compounds can be applied as photosensitizers (photocharge separators) to various nonsilver light-image formation methods, and can be used as photocatalysts or photo hydrogen generators.

The term "light absorption intensity" used in the present invention refers to the areal intensity of light absorption by sensitizing dyes per unit grain surface area, and defined as the value obtained by integrating the optical density $\log(I_0/(I_0-I))$ with respect to wave number ($cm^{-1}$) wherein $I_0$ stands for the quantity of light incident on the unit surface area of grain and I stands for the quantity of light absorbed by sensitizing dyes present on the unit grain surface. The integration interval therein is from 5,000 $cm^{-1}$ to 35,000 $cm^{-1}$.

It is appropriate for the silver halide photographic emulsion relating to the present invention to contain silver halide grains at least 50%, based on projected area, of which are silver halide grains having a light absorption intensity of at least 100 when they exhibit the spectral absorption maximum at a wavelength of not shorter than 500 nm or silver halide grains having a light absorption intensity of at least 60 when they exhibit the spectral absorption maximum at a wavelength of shorter than 500 nm. In the case where the grains exhibit their spectral absorption maximum at a wavelength of 500 nm or longer, the light absorption intensity is preferably at least 150, more preferably at least 170, particularly preferably at least 200; while when the grains exhibit their spectral absorption maximum at a wavelength of shorter than 500 nm the light absorption intensity is preferably at least 90, more preferably at least 100, particularly preferably at least 120. The light absorption intensity has no particular upper limit, but the upper limit thereof is preferably 2,000 or less, more preferably 1,000 or less, particularly preferably 500 or less.

As to the grains exhibiting their spectral absorption maximum at a wavelength of shorter than 500 nm, it is preferable that the wavelength of their spectral absorption maximum be not shorter than 350 nm.

As an example of the measurement method of light absorption intensity, mention may be made of a method of using a microspectrophotometer. The microspectorphotometer is an instrument enabling the absorption spectrum measurement of an analyte having a minute area, and makes it possible to measure the transmission spectrum of one grain. For the measurement of absorption spectrum of one grain by microspectrophotometry the report by Yamashita et al. (*A Collection of Abstracts of Lectures in* 1996 *Annual Meeting of Japanese Photographic Society*, page 15) can be referred to. Although the absorption intensity per grain can be determined from the absorption spectrum of one grain, the light penetrating a grain is absorbed at the two surfaces, the upper and lower surfaces, of the grain. Accordingly, the absorption intensity per unit area of grain surface can be determined as ½ of the absorption intensity per grain. The wave number interval for integrating the absorption spectrum is, by definition, from 5,000 $cm^{-1}$ to 350,000 $cm^{-1}$, but there is nothing wrong in practice with integrating the absorption spectrum from the wave number greater than the absorption band of sensitizing dyes by about 500 $cm^{-1}$ to the wave number smaller than the absorption band of sensitizing dyes by about 500 $cm^{-1}$.

Further, the light absorption intensity is a value uniquely determined by the oscillator strength of a sensitizing dye used and the number of the molecules adsorbed per unit area, and so if the oscillator strength of a sensitizing dye used, the quantity of dye adsorbed and the grain surface area are determined respectively, these values can be converted into the light absorption intensity.

The oscillator strength of a sensitizing dye can be determined experimentally as the value proportional to the areal intensity of absorption by a sensitizing dye solution (optical density×$cm^{-1}$), so that when the areal intensity of absorption by a 1M solution of sensitizing dye is represented by A (optical density×$cm^{-1}$), the quantity of sensitizing dye adsorbed is represented by B (mole/mole Ag) and the grain surface area is represented by C ($m^2$/mole Ag), the light absorption intensity can be determined by the following formula, with an error of the order of about 10%:

$$0.156 \times A \times B/C$$

In other words, the value of the light absorption intensity calculated from the above formula is practically the same as the value determined by the measurement based on the foregoing definition (or the value obtained by integrating $\log(I_0/(I_0-I))$ with respect to wave number ($cm^{-1}$)).

As methods of increasing the light absorption intensity, there are a method of causing dye chromophores to adsorb to the grain surface in more than one layer, a method of heightening the molecular absorption constants of dyes, and a method of lessening the area occupied by dyes. Any of these methods can be adopted, but it is preferable to adopt the method of causing dye chromophores to adsorb to the grain surface in more than one layer.

The expression "a state in which dye chromophores are adsorbed to the grain surface in more than one layer" means that dye molecules bound to the vicinity of each silver halide grain are present in more than one layer, and does include dye molecules present in a dispersion medium. And the expression "more than one layer" used herein is intended to include the cases where the dye chromophores are coupled to dye molecules adsorbed on the grain surface via covalent bonds as in the present invention. In these cases, it is required that spectral sensitization be effected by the dyes adsorbed indirectly to the grain surface; as a result, it becomes necessary to cause excitation energy transfer from the dye molecules adsorbed indirectly to silver halide grains to the dye molecules adsorbed directly to the silver halide grains. Therefore, the cases in which the transfer of excitation energy requires passing at least 10 stages are undesirable because the final transfer efficiency of excitation energy becomes low. As one example of such cases, mention may be made of the case of polymeric dyes disclosed in Japanese Patent Application (Laid-Open) No. 113239/1990, wherein most of dye chromophores are present in a dispersion medium and the transfer of excitation energy requires passing at least 10 stages.

It is appropriate that the dye chromophores be adsorbed to silver halide grains in at least 1.5 layers, preferably at least 1.7 layers, particularly preferably at least two layers.

The phrase "the state in which dye chromophores are adsorbed to the surface of each silver halide grain in more than one layer" refers to a state that, when the saturated amount of adsorption per unit surface area achieved by a dye having the smallest occupied area on the surface of each silver halide grains among the sensitizing dyes added to the emulsion is defined as a one-layer saturation coverage, the amount of dye chromophores adsorbed per unit surface area is greater than the one-layer saturation coverage. The number of adsorption layers signifies the amount of adsorption on a basis of the one-layer saturation coverage. In the case of a dye in which dye chromophores are coupled to each other via covalent bonds, the dye occupation areas of individual dyes in an uncoupled state can be taken as the reference.

The dye occupation area can be determined from adsorption isotherm, which shows relations between free dye concentrations and amounts of adsorbed dyes, and surface areas of grains. The adsorption isotherm can be determined by reference to A. Herz, *Adsorption from Aqueous Solution*, Advances in Chemistry Series No. 17, page 173 (1968).

The amount of sensitizing dye molecules adsorbed to emulsion grains can be determined using either of the following two methods. In one method, an emulsion containing dye-adsorbed grains is put through a centrifuge, and thereby separated into the grains and an aqueous gelatin solution as supernatant liquor. From spectrophotometry of the supernatant liquor, the concentration of unadsorbed dye molecules is determined. Thus, the amount of adsorbed dye molecules can be evaluated by deducting the amount of the unadsorbed dye molecules from the amount of the dye added. In the other method, the emulsion grains precipitated are dried, and a fixed weight of the precipitate is dissolved in a 1:1 mixture of methanol and an aqueous solution of sodium sulfate and subjected to spectrophotometry, thereby determining the amount of adsorbed dye. When two or more kinds of sensitizing dyes are used, the adsorption amount of each individual dye can be determined, e.g., by high-performance liquid chromatography.

Although the dye occupation area can be determined experimentally, the area occupied by one molecule of a generally used sensitizing dye is of the order of about 80 $Å^2$. Therefore, an approximate number of adsorption layers can also be evaluated assuming for convenience sake that every dye has a dye molecule-occupied area of 80 $Å^2$.

In the silver halide photographic emulsions containing the present compounds as sensitizing dyes, the suitable wavelength interval between the shortest wavelength and the longest wavelength corresponding to 50% of the maximum of spectral absorptance attributed to the sensitizing dyes, Amax, and that corresponding to 50% of the maximum of spectral sensitivity conferred by the sensitizing dyes, Smax, are each 120 nm or below, preferably 100 nm or below.

Further, the wavelength interval between the shortest wavelength and the longest wavelength corresponding to 80% of Amax and that corresponding to 80% of Smax are each at least 20 nm, and desirably 100 nm or less, more desirably 80 nm or less, especially desirably 50 nm or less.

Furthermore, the suitable wavelength interval between the shortest wavelength and the longest wavelength corresponding to 20% of Amax and that corresponding to 20% of Smax are each 180 nm or less, preferably 150 nm or less, more preferably 120 nm or less, particularly preferably 100 nm or less.

The longest wavelength showing the spectral absorptance corresponding to 50% of Amax or Smax is preferably from 460 nm to 510 nm, or from 560 nm to 610 nm, or from 640 nm to 730 nm.

In the cases where dye chromophores are adsorbed to silver halide grains in multiple layers, not only the dye chromophore adsorbed directly to silver halide grains, or the so-called first-layer dye chromophore, but also the dye chromophores forming the second and higher-order layers have no particular restrictions as to their reduction potentials and oxidation potentials. However, from the viewpoints of acceleration of electron transfer from the first-layer dye to the second and higher-layer dyes and prevention of reverse electron transfer, it is appropriate that the reduction potential of the first-layer dye chromophore be more electropositive, compared with the value obtained by deducting 0.2 V from the reduction potential of dye chromophores forming the second and higher-order layers. Preferably, the reduction potential of the first-layer dye chromophore is more electropositive for the reduction potential of the second and higher-layer dye chromophores.

Measurements of reduction potential and oxidation potential can be made in various ways. Preferably, the measurements are performed by phase discrimination type second harmonic alternating-current polarography, and thereby accurate values can be determined. Additionally, the potential measurements by phase discrimination type second harmonic alternating-current polarography are described in *Journal of Imaging Science*, volume 30, page 27 (1986).

The dye chromophores forming the second and higher-order layers are preferably luminous dyes. As to the kinds of luminous dyes, it is preferable that the luminous dyes have framework structures similar to those of dyes used for dye laser. These are sorted through in, e.g., Mitsuo Maeda, *Laser Kenkyu* (Laser studies), vol. 8, pp. 649, 803 and 958 (1980), supra, vol. 9, p. 85 (1981), and F. Sehaefer, *Dye Lasers*, Springer (1973).

Further, it is advantageous that the wavelength at which the dye chromophore forming the first layer exhibits its absorption maximum in a silver halide photographic material is longer than those at which the dye chromophores forming the second and higher-order layers exhibit their absorption maxima. Furthermore, from the viewpoint of efficiency in energy transfer from dyes of the second and higher-order layers to the dye of first layer, it is beneficial that the luminescence of the dye chromophores forming the second and higher-order layers overlaps with the absorption of the dye chromophore forming the first layer. In addition, it is advantageous that the dye chromophore of the first layer takes the form of J-aggregate. Moreover, for effecting absorption and spectral sensitivity in the desired wavelength region, it is favorable that the dye chromophores of the second and higher-order layers take the form of J-aggregates.

The suitable efficiency in energy transfer of excitation energy of the second-layer dye to the first-layer dye is at least 30%, preferably at least 60%, particularly preferably at least 90%. The term "excitation energy of the second-layer dye" used herein refers to the energy the second-layer dye has when it enters an excited state by absorbing light energy. The energy transfer of the excitation energy one molecule has to the other molecule is thought to take place through an excited electron transfer mechanism, a Forster Model energy transfer mechanism or a Dextor Model energy transfer mechanism. Therefore, it is appropriate that the present multi-layer adsorption system also satisfy conditions for causing efficient excitation energy transfer which are inferred from these mechanisms. In particular, it is advantageous to meet conditions for causing the Forster Model energy transfer mechanism.

The efficiency in energy transfer from the second-layer dye to the first-layer dye can be evaluated as a ratio of the spectral sensitization efficiency at the time when the second-layer dye is excited to the spectral sensitization efficiency at the time when the first-layer dye is excited.

The meanings of the terms used in the present invention are explained below.

Dye occupation area: The area occupied by one molecule of dye. This area can be determined experimentally from adsorption isotherm. In the case of dyes in which dye chromophores are coupled to each other via covalent bonds, occupation areas of individual dyes in the uncoupled sate are adopted as the references. Rough estimation thereof is 80 $Å^2$.

One-layer saturation coverage: The amount of a dye adsorbed per unit grain surface area at the time the dye covers grains in one saturated layer, or the reciprocal of the area occupied by the smallest dye of all sensitizing dyes added to the emulsion.

Adsorption in more than one layer (i.e., in multi-layer): The state that the amount of dye chromophores adsorbed per unit grain surface area is greater than the one-layer saturation coverage. Additionally, since the term "adsorption in more than one layer" used in the present invention is defined above, the case where a dye having two dye chromophores coupled via covalent bonds adsorbs in one layer portion refers to double-layer adsorption.

Number of adsorption layers: The amount of dye chromophores adsorbed per unit grain surface area, expressed on a basis of one-layer saturation coverage. In the case of a compound having two dye chromophores coupled via covalent bonds, the number of adsorption layers is defined as twice as much as the amount adsorbed. For instance, if a dye having two dye chromophores coupled via covalent bonds has the same dye occupation area and the same amount adsorbed as a certain dye of uncoupled model, the number of adsorption layers stands at 2.

EXAMPLE

The present invention will now be illustrated in greater detail by reference to the following examples, but it should be understood that these examples are not to be construed as limiting the scope of the present invention in any way.

Example 1

Synthesis of Present Compound No. 5:

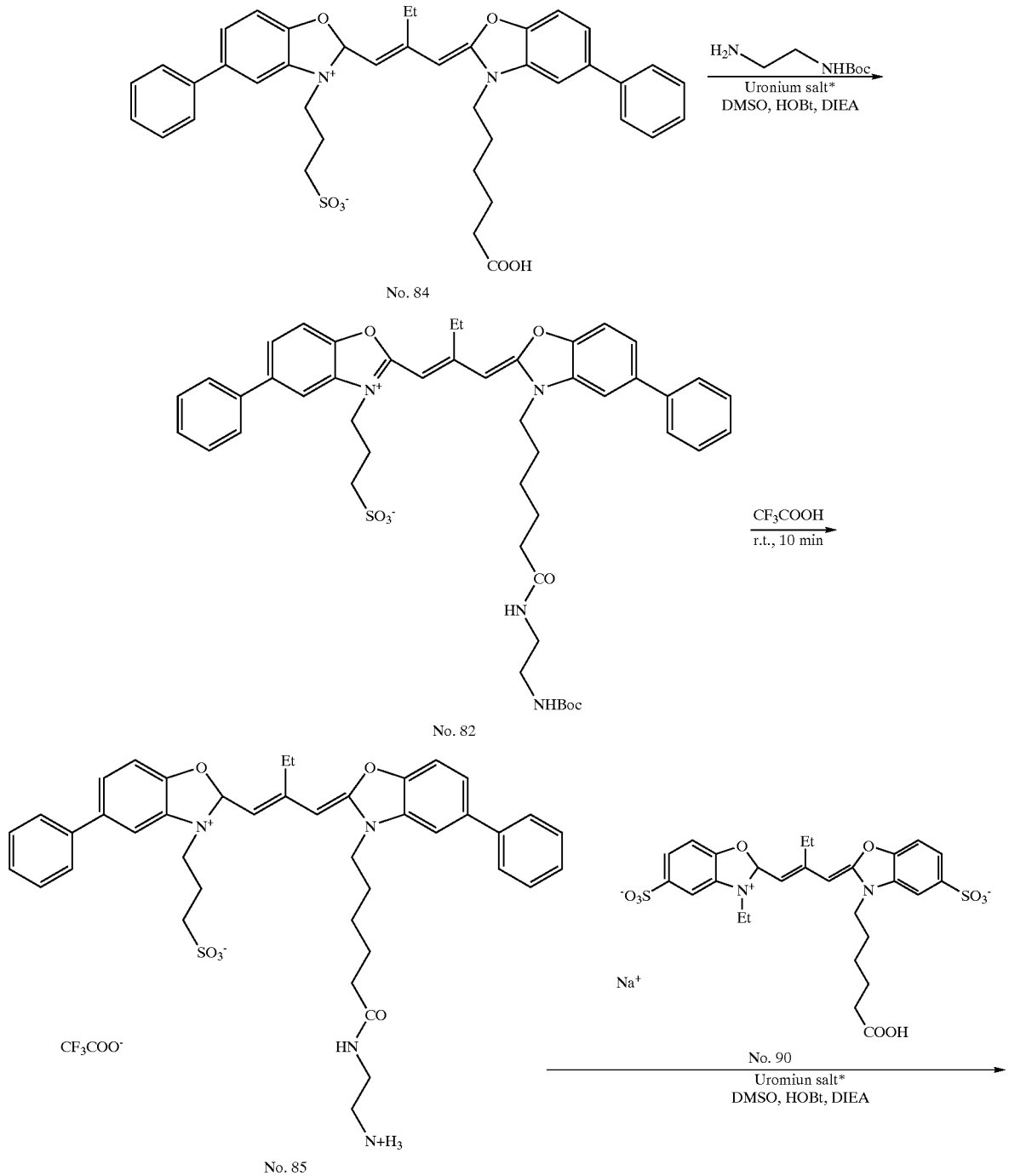

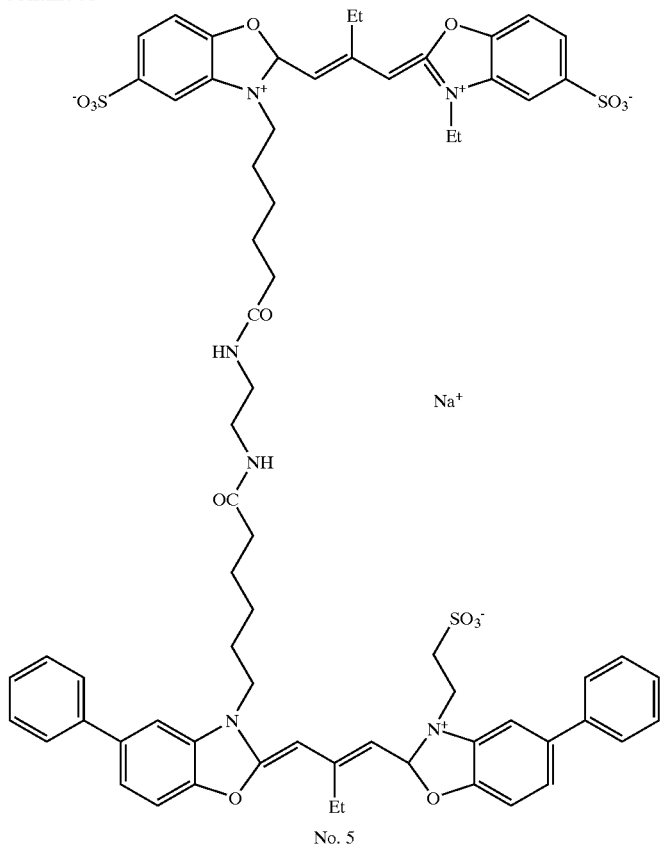

No. 5

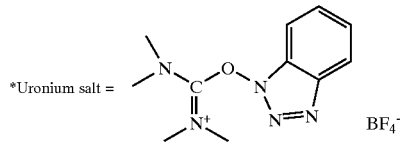
*Uronium salt =

In DMSO, 4.2 g of Compound No. 94 synthesized in a usual manner and 0.93 g of 1-hydroxybenzotriazole (HOBt) were dissolved, and stirred for 10 minutes at an external temperature of 60° C. Thereto, 1.0 g of tert-butyl N-(2-aminoethyl)carbamate and 2.4 g of O-(benzotriazole-1-yl)-N,N.N',N'-tetramethyluronium tetrafluoroborate were added in succession, and further 4.35 ml of diisopropylethylamine (DIEA) was added, followed by stirring for 1.5 hours at 60° C.

Thereafter, the reaction solution was admixed with ethyl acetate and hexane to precipitate crystals. The crystals were filtered off, and dried. Thus, 3.5 g of Compound No. 82 was obtained. The structure of the compound obtained was ascertained by measurements of NMR and MS spectra and elemental analysis.

The other compounds represented by the present formula (5) can be synthesized in the same manner as described above.

Then, 1.0 g of Compound No. 82 obtained by the aforedescribed method was put in a flask, and thereto 10 ml of trifluoroacetic acid was added, followed by stirring for 10 minutes at room temperature. Thereto, ethyl acetate was further added to deposit crystals. The crystals were filtered off, and dried. Thus, 0.8 g of Compound No. 65 was obtained. The structure of this compound was ascertained by measurements of NMR and MS spectra and elemental analysis.

The other compounds represented by the present formula (3) can also be synthesized by the same method as described above.

Furthermore, 0.5 g of Compound No. 65 obtained by the foregoing method, 0.8 g of Compound No. 90 synthesized separately in an usual method, and 1.0 g of 1-hydroxybenzotriazole were dissolved in DMSO, and stirred for 10 minutes at an external temperature of 60° C. Thereto, 0.56 g of O-(benzotriazole-1-yl)-N,N.N',N'-tetramethyluronium tetrafluoroborate and 1.3 ml of diisopropylethylamine (DIEA) were added in succession, followed by stirring for 1.5 hours at 60° C.

Thereafter, the reaction solution was admixed with acetone to deposit crystals. The crystals were filtered off, and dissolved completely in methanol. Thereto, a solution prepared in advance by dissolving 0.2 g of sodium acetate in methanol was added, resulting in separation of crystals. These crystals were filtered off to yield a crude product. The crude product was purified by Cefadex (LH-20, methanol solvent) column chromatography, and then dried. Thus, 0.25 g of Compound No. 5 was obtained. The structure of the compound thus obtained was ascertained by measurements of NMR and MS spectra and elemental analysis.

The other compounds represented by the present formula (1) can be synthesized by the same method as described above.

Example 2

(1) Emulsion-making:

<Preparation of Seed Emulsion>

A solution containing 0.017 g of KBr and 0.4 g of oxidation-processed gelatin having an average molecular weight of 20,000 in 1164 ml of water was kept at 35° C. with stirring. Thereto, an aqueous solution of $AgNO_3$ (1.6g), an aqueous solution of KBr and an aqueous solution of oxidation-processed gelatin having an average molecular weight of 20,000 (2.1 g) were added over a 48-second period using the triple jet method. At this time, the silver potential was kept at 13 mV with reference to the saturated calomel electrode. After the silver potential was changed to −66 mV by addition of an aqueous solution of KBr, the resulting solution was heated up to 60° C. Thereto, 21 g of succinated gelatin having an average molecular weight of 100,000 was added, and then an aqueous solution of NaCl (5.1 g) was added. Further, an aqueous solution of $AgNO_3$ (206.3 g) and an aqueous solution of KBr were added over a 61-minute period at an increased flow rate in accordance with a double jet method. During the addition, the Ag potential was kept at −44 mV with reference to the saturated calomel electrode. After removal of soluble salts, the resulting solution was admixed with succinated gelatin having an average molecular weight of 100,000, and adjusted to pH 5.8 and pAg 8.8 at 40° C. Thus, a seed emulsion was prepared. The thus prepared seed emulsion contained 1 mole of Ag and 80 g of gelatin per kg of emulsion. The emulsion grains contained therein were tabular grains having an average equivalent circle diameter of 1.46 μm, a variation coefficient of 28% with respect to the equivalent circle diameter, an average thickness of 0.046 μm and an average aspect ratio of 32.

<Formation of Core>

1,200 ml of an aqueous solution containing 134 g of the seed emulsion (a), 1.9 g of KBr and 22 g of succinated gelatin having an average molecular weight of 100,000 was kept at 75° C. with stirring. Just before addition thereto, an aqueous solution of $AgNO_3$ (43.9 g), an aqueous solution of KBr and an aqueous solution of gelatin having molecular weight of 20,000 were mixed in a separate chamber equipped with the magnetic coupling induction type stirrer disclosed in Japanese Patent Application (Laid-Open) No. 43570/1998. The mixture prepared was added to the solution kept at 75° C. over a period of 25 minutes, while keeping an Ag potential at −40 mV with reference to the saturated calomel electrode.

<Formation of First Shell>

To the emulsion after the formation of the core grains was added over a 20-minute period a solution prepared in a separate chamber of the same type as described above just before the addition by mixing an aqueous solution of $AgNO_3$ (43.9 g), an aqueous solution of KBr and an aqueous solution of gelatin having molecular weight of 20,000. At this time, the Ag potential was also kept at −40 mV with reference to the saturated calomel electrode.

<Formation of Second Shell>

To the emulsion after the formation of the first shell was added over a 17-minute period a solution prepared in a separate chamber of the same type as described above just before the addition by mixing an aqueous solution of $AgNO_3$ (42.6 g), an aqueous solution of KBr and an aqueous solution of gelatin having molecular weight of 20,000. At this time, the Ag potential was kept at −20 mV with reference to the saturated calomel electrode. Thereafter, the emulsion obtained was cooled to 55° C.

<Formation of Third Shell>

After the formation of the second shell, the silver potential of the emulsion obtained was adjusted to −55 mV, and thereto was added over a 5 minutes a solution prepared in a separate chamber of the same type as mention above just before the addition by mixing an aqueous solution of $AgNO_3$ (7.1 g), an aqueous solution of KBr (6.9 g) and an aqueous solution of gelatin having molecular weight of 20,000.

<Formation of Fourth Shell>

To the emulsion after the third shell, an aqueous solution of $AgNO_3$ (66.4 g) and an aqueous solution of KBr were added at a constant flow rate over a 30-minute period in accordance with a double jet method. On the way, potassium iridium hexachloride and hexacyanoferrate (II) were further added. At this time, the silver potential was kept at 30 mV with reference to the saturated calomel electrode. The resulting emulsion was washed in a usual manner, admixed with gelatin, and adjusted to pH 5.8 and pAg 8.8 at 40° C. The emulsion thus obtained was referred to as Emulsion (b). The grains in Emulsion (b) were tabular grains having an average projected area diameter of 3.3 μm, a variation coefficient of 21% with respect to the projected area diameter, an average thickness of 0.090 μm and an average aspect ratio of 37. Additionally, the tabular grains having equivalent circle diameters of 3.3 μm or above and thicknesses of 0.090 μm or below constituted at least 70% of the total projected area. The one-layer saturation coverage was $1.45 \times 10^{-3}$ mole/mole Ag when the dye occupation area was taken as 80 $Å^2$.

Emulsion (b) was heated up to 56° C. Thereto, a comparative dye illustrated below, Dye S-1, was added in an amount of $1.2 \times 10^{-3}$ mol/mol Ag, and the resulting emulsion was chemically sensitized by addition of C-5, potassium thiocyanate, chloroauric acid, sodium thiosulfate and N,N-dimethylselenourea under optimum conditions. Thereto, $2.5 \times 10^{-4}$ mole/mole Ag of Dye S-1 was further added, and stirred for 60 minutes. Thus, an emulsion for Comparative Example 1 was prepared.

(2) Measurements of Light Absorption Intensity and Amount Adsorbed:

The measurement of light absorption intensity per unit area was made as follows.

The emulsion obtained was coated in a thin layer on a slide glass, and transmission and reflection spectra of individual emulsion grains in the coating were measured with a microspectrophotometer MSP65 made by Carl Zweiss A. G., thereby determining the absorption spectrum. Herein, the transmission spectrum of the grain-free part in the coating was taken as a reference transmission spectrum, and the reflection spectrum of silicon carbide having already known reflectance was employed as a reference reflection spectrum. The measured part was a circular aperture part having a diameter of 1 μm, and the measuring position was adjusted so that the aperture part didn't overlap with the outline of a grain. The transmission and reflection spectra of each grain were measured in the wavelength region of 14,000 $cm^{-1}$ (714 nm) to 28,000 $cm^{-1}$ (357 nm), and the absorption spectrum was determined taking the absorptance A as 1−T (transmittance)−R (reflectance). The absorptance obtained by deducting the absorptance of silver halide from the absorptance A was represented by A', and one-half the value obtained by integrating $-\log(1-A')$ with respect to wave number ($cm^{-1}$) was defined as the light absorption intensity per unit surface area. The integrating range therein was from 14,000 $cm^{-1}$ to 28,000 $cm^{-1}$. In the spectral measurements, a tungsten lamp was used as a light source, and the light source voltage was set at 8 V. In order to minimize the damage to dyes resulting from irradiation with light, a primary-side monochrometer was used, and the spacing between wavelengths was adjusted to 2 nm and the slit width was adjusted to 2.5 nm. Absorption spectra and light absorption intensities of 200 grains individually were determined.

The amount of dyes adsorbed was determined as follows.

A liquid emulsion prepared was settled using a centrifuge for 10 minutes at 10,000 rpm. The sediment obtained was freeze-dried, and then 0.05 g of the dried sediment was added to 25 ml of a 25% aqueous solution of sodium thiosulfate, and further methanol was added thereto to adjust the total volume to 50 ml. This solution was analyzed by high-performance liquid chromatography to determine the dye concentration. The number of dye adsorption layers was evaluated from the thus determined amount of dyes adsorbed and the one-layer saturation coverage.

(3) Production of Coating Samples:

An emulsion layer and a protective layer as shown in Table 1 were coated on a subbing layer-provided triacetyl cellulose film, thereby producing a Sample No. 101. Further, Sample Nos. 102 and 103 were produced by using the present compounds respectively in equimolecular amounts in place of Comparative Compound S-1.

TABLE 1

Conditions for Coating Emulsion (1) Emulsion layer

| Emulsion . . . Emulsion (b) | (Dyes used are shown in Table 2) |
|---|---|
| Coupler | ($1.65 \times 10^{-3}$ mole/m²) |

[Chemical structure shown]

| Tricresyl phosphate | (1.45 g/m²) |
|---|---|
| Gelatin | (2.30 g/m²) |

(2) Protective layer

| 2,4-Dichloro-6-hydroxy-s-triazine sodium salt | (0.08 g/m²) |
|---|---|
| Gelatin | (1.80 g/m²) |

These samples were each subjected to exposure for sensitometry (1/100 second), and then to the color photographic processing described below.

Processing Process:

| Step | Processing time | Processing temp. | Replenisher volume | Tank volume |
|---|---|---|---|---|
| Color development | 2 min. 45 sec. | 38° C. | 33 ml | 20 l |
| Bleaching | 6 min. 30 sec. | 38° C. | 25 ml | 40 l |
| Washing | 2 min. 10 sec. | 24° C. | 1,200 ml | 20 l |
| Fixing | 4 min. 20 sec. | 38° C. | 25 ml | 30 l |
| Washing (1) | 1 min. 05 sec. | 24° C. | counter-current plumbing system from (2) to (1) | 10 l |
| Washing (2) | 1 min. 00 sec. | 24° C. | 1,200 ml | 10 l |
| Stabilization | 1 min. 05 sec. | 38° C. | 25 ml | 10 l |
| Drying | 4 min. 20 sec. | 55° C. | | |

Each of the replenisher volumes shown above is per processed area 35 mm wide and 1 m long.

The compositions of the processing solutions used in the foregoing steps are as follows:

|  | Mother liquor | Replenisher |
|---|---|---|
| (Color developer) | | |
| Diethylenetriaminepentaacetic acid | 1.0 g | 1.1 g |
| 1-Hydroxyethylidene-1,1-diphosphonic acid | 3.0 g | 3.2 g |
| Sodium sulfite | 4.0 g | 4.4 g |
| Potassium carbonate | 30.0 g | 37.0 g |
| Potassium bromide | 1.4 g | 0.7 g |
| Potassium iodide | 1.5 mg | — |
| Hydroxylamine sulfate | 2.4 g | 2.8 g |
| 4-[N-Ethyl-N-β-hydroxyethylamino]-2-methylaniline sulfate | 4.5 g | 5.5 g |
| Water to make | 1.0 l | 1.0 l |
| pH adjusted to | 10.05 | 10.05 |
| (Bleaching Solution) | | |
| Sodium iron (III) ethylenediaminetetraacetate trihydrate | 100.0 g | 120.0 g |
| Disodium ethylenediaminetetraacetate | 10.0 g | 11.0 g |
| Ammonium bromide | 140.0 g | 160.0 g |
| Ammonium nitrate | 30.0 g | 35.0 g |
| Aqueous ammonia (27%) | 6.5 ml | 4.0 ml |
| Water to make | 1.0 l | 1.0 l |
| pH adjusted to | 6.0 | 5.7 |
| (Fixing Solution) | | |
| Sodium ethylenediaminetetraacetate | 0.5 g | 0.7 g |
| Sodium sulfite | 7.0 g | 8.0 g |
| Sodium hydrogensulfite | 5.0 g | 5.5 g |
| Aqueous ammonium thiosulfate solution (70%) | 170 ml | 200 ml |
| Water to make | 1.0 l | 1.0 l |
| pH adjusted to | 6.7 | 6.65 |
| (Stabilizing Solution) | | |
| Formaldehyde (37%) | 2.0 ml | 3.0 ml |
| Polyoxyethylene-p-monononylphenyl ether (average polymerization degree: 10) | 0.3 g | 0.45 g |
| Disodium ethylenediaminetetraacetate | 0.05 g | 0.08 g |
| Water to make | 1.0 l | 1.0 l |
| pH adjusted to | 5.8–8.0 | 5.8–8.0 |

Density measurements of the processed samples were made via a blue filter, and thereby the sensitivity and fog of each sample were evaluated.

Therein, the sensitivity was defined as the reciprocal of the exposure amount providing a density higher than the fog density by 0.2. The sensitivities set forth in Table 2 are shown as relative values, with Sample No. 101 being taken as 100. The measurement results of light absorption intensity of the comparative compound- or the present compound-adsorbed emulsion grains used in each sample and sensitivity of each sample are shown in Table 2. Additionally, each of light absorption intensities set forth in Table 2 is an average value of 200 grains determined by microspectroscopy. As to both light absorption intensity and sensitivity, the values of Comparative Sample No. 101 are adopted as standards. And the light absorption intensity of Comparative Sample No. 101 was found to be 56.

TABLE 2

| Sample No. | Compound | Light absorption intensity | Sensitivity | note |
|---|---|---|---|---|
| 101 | S-1 | 100 (standard) | 100 (standard) | comparison |
| 102 | No. 5 | 175 | 162 | invention |

TABLE 2-continued

| Sample No. | Compound | Light absorption intensity | Sensitivity | note |
|---|---|---|---|---|
| 103 | No. 6 | 161 | 149 | invention |

S-1

[Structure of S-1 compound showing two benzoxazole rings connected by -CH=C(C2H5)-CH= methine bridge, with Cl substituents, N+(CH2)3SO3- and N(CH2)3SO3- Na+ groups]

C-5

[Structure of C-5: pyrimidine-triazole fused ring system with CH3 and OH substituents]

As can be seen from Table 2, the present compounds enabled improvement in light absorptance, compared with the comparative compound S-1, because they take a multilayer structure; as a result, the sensitivity was increased. In the case of Sample No. 102 using the present compound No. 5, the number of absorption layers was 1.96 and, in the case of Sample No. 103 using the present compound No. 6, the number of absorption layers was 1.98. In other words, the present compound adsorbed to emulsion grains takes a structure close to a double-layer structure. By the way, the areal intensity of light absorption by Sample No. 102 was 1.89 times higher than that of Sample No. 101 using the comparative compound S-1. Additionally, these results indicate that the excitation of the second-layer dye by light contributes to a sensitivity increase via energy transfer or electron transfer to the first-layer dye.

Example 3

Comparisons similar to those in Example 2 were performed in a system of the color negative photosensitive material disclosed in Example 5 of Japanese Patent Application (Laid-Open) No. 29904/1996. Therein, the sensitivity of the photosensitive material using the present compound No. 15 was high sensitivity of 177 when the sensitivity of the blue-sensitive layer of the photosensitive material using the comparative compound S-1 was taken as 100 (standard). Comparisons similar to those in Example 2 were further made in a system of the instant photographic material disclosed in Example 1 of Japanese Patent Application (Laid-Open) No. 28442/2000. Therein, the sensitivity of the photosensitive material using the present compound No. 16 was high sensitivity of 171 when the sensitivity of the blue-sensitive layer of the photographic material using the comparative compound S-1 was taken as 100 (standard). Furthermore, in each of systems of the color reversal photosensitive materials disclosed in Example 1 of Japanese Patent Application (Laid-Open) Nos. 92601/1995 and 160828/1995, the color paper disclosed in Example 1 of Japanese Patent Application (Laid-Open) No. 347944/1994, the X-ray sensitive material disclosed in Example 1 of Japanese Patent Application (Laid-Open) No. 122954/1996, the heat-developable photosensitive material disclosed in Example 1 of Japanese Patent Application (Laid-Open) No. 281785/2001, and the photosensitive material for graphic arts as disclosed in Example 1 of Japanese Patent Application (Laid-Open) No. 292512/1996, it has been proved that the sensitive materials using the present compounds were each higher in sensitivity than the sensitive material using the comparative compound. In addition, it has been found also in each of those systems that the present compounds were useful because they had higher light absorption intensities and were greater in number of chromophore absorption layers.

EFFECT OF THE INVENTION

Novel methine dyes and synthesis methods thereof are provided by the present invention.

By use of the present compound containing methine dyes coupled to each other, a multilayer structure is formed to enhance light absorptance, thereby ensuring high sensitivity in silver halide photographic materials.

The entitle disclosure of each and every foreign patent application from which the benefit of foreign priority has been claimed in the present application is incorporated herein by reference, as if fully set forth herein.

While the invention has been described in detail and with reference to specific embodiments thereof, it will be apparent to one skilled in the art that various changes and modifications can be made therein without departing from the spirit and scope thereof.

What is claimed is:

1. A compound represented by formula (1):

$$\text{Dye1-}(L_1\text{-(Dye2)}_{m1})_{m2} \, (CI_1)_{y1} \quad (1)$$

wherein $L_1$ represents a linkage group represented by formula (2), m1 represents an integer of 1 to 5, m2 represents an integer of 1 to 5, Dye1 represents a first chromophore, Dye 2 represents a second chromophore, $CI_1$ represents an ion for neutralization of electric charge, and y1 represents a number of the ions required for neutralization of electric charges;

$$-G_1\text{-}A_1\text{-}Y_1\text{-}G_2\text{-}Y_2\text{-}A_2\text{-}G_3- \quad (2)$$

wherein $A_1$ and $A_2$ each individually represent a carbonyl group or a sulfonyl group, $Y_1$ and $Y_2$ each individually represent —O—, —S— or —$NR_1$—, $R_1$ represents a hydrogen atom, an alkyl group, an alkenyl group, an aryl group or a heterocyclic group, and $G_1$, $G_2$ and $G_3$ each individually represent a divalent linkage group, and wherein both Dye1 and Dye2 are cyanine or merocyanine chromophores which each have at least one benzoxazole nucleus.

2. A method of manufacturing a compound of formula (1) as defined in claim 1 by causing a reaction between a compound represented by formula (3) and a compound represented by formula (4):

$$\text{Dye3-}G_4\text{-}A_3\text{-}Y_4\text{-}G_5\text{-}Y_4\text{-}H \, (CI_2)_{y2} \quad (3)$$

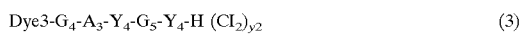

wherein $\text{Dye}_3$ represents a chromophore, $Y_4$ represents —NH—, —$NH_2^+$—, —S— or —O—, $A_3$ represents a carbonyl group or a sulfonyl group, $Y_3$ represents —O—, —S— or —$NR_1$—, $R_1$ represents a hydrogen atom, an alkyl group, an alkenyl group, an aryl group or a heterocyclic group, $G_4$ and $G_5$ each individually represent a divalent linkage group, $CI_2$ represents an ion for neutralization of electric charge, and y2 represents a number of the ions required for neutralization of electric charges $$\text{Dye4-}G_6\text{-}A_4\text{-}Y_5 \, (CI_3)_{y3} \quad (4)$$

wherein Dye4 represents a chromophore, $A_4$ represents a carbonyl group or a sulfonyl group, $G_6$ represents a divalent linkage group, $Y_5$ represents a hydroxyl group, a halogen atom, an alkoxy group, an aryloxy group, an acyloxy group, an alkyl- or arylsulfonyloxy group, an alkyl- or aryloxycarbonyloxy group, an imidyloxycarbonyloxy group or a heterocyclic group, $CI_3$ represents an ion for neutralization of electric charge, and y3 represents a number of the ions required for neutralization of electric charges.

3. The compound as claimed in claim 1, wherein both Dye1 and Dye2 are cyanine chromophores.

4. The compound as claimed in claim 1, wherein Dye1 is a cyanine chromophore and Dye2 is a merocyanine chromophore.

* * * * *